US008173700B2

(12) United States Patent
Frank et al.

(10) Patent No.: US 8,173,700 B2
(45) Date of Patent: May 8, 2012

(54) SALTS OF SUBSTITUTED ALLOPHANATES AND THEIR USE IN DRUGS

(75) Inventors: Robert Frank, Aachen (DE); Ruth Jostock, Stolberg (DE); Hans Schick, Berlin (DE); Fritz Theil, Berlin (DE); Olga Groeger, Berlin (DE); Rene Kudick, Gruenheide (DE); Helmut Sonnenschein, Berlin (DE); Birgitta Henkel, Berlin (DE)

(73) Assignee: Gruenenthal GmbH, Aachen (DE)

( * ) Notice: Subject to any disclaimer, the term of this patent is extended or adjusted under 35 U.S.C. 154(b) by 979 days.

(21) Appl. No.: 11/914,574

(22) PCT Filed: May 17, 2006

(86) PCT No.: PCT/EP2006/004657
§ 371 (c)(1),
(2), (4) Date: Jul. 2, 2008

(87) PCT Pub. No.: WO2006/122772
PCT Pub. Date: Nov. 23, 2006

(65) Prior Publication Data
US 2009/0062383 A1     Mar. 5, 2009

(30) Foreign Application Priority Data
May 18, 2005   (DE) .......................... 10 2005 023 588

(51) Int. Cl.
*C07D 207/09*      (2006.01)
*C07D 307/16*      (2006.01)
*C07C 271/18*      (2006.01)
*A61K 31/325*      (2006.01)
*A61K 31/341*      (2006.01)

(52) U.S. Cl. ........ 514/471; 514/428; 514/506; 548/567; 549/473; 549/496; 560/159

(58) Field of Classification Search ........................ None
See application file for complete search history.

(56) References Cited

U.S. PATENT DOCUMENTS
4,684,728 A     8/1987   Moehring et al.
5,494,922 A     2/1996   Brown et al.
2004/0204486 A1  10/2004  Hogestatt et al.

FOREIGN PATENT DOCUMENTS
DE         101 31 462 A1      1/2003

OTHER PUBLICATIONS

Golub et al., Science, 286, 531-537, Oct. 15, 1999.*
Blohm, Herbert W. et al., "Allophanates", Chem. Rev., 51(3), 471-504, Dec. 1952.*
Alfonso R Gennaro, Table of Contents, Pharmaceutical Preparations and Their Manufacture, Pharmaceutical Sciences, 1985 Mack Publishing Company, Easton, Pennsylvania, (Four (4) pages).
David Dubuisson et al., "The Formalin Test: A Quantitative Study of the Analgesic Effects of Morphine, Meperidine, and Brain Stem Stimulation in Rats and Cats", Pain, Department of Psychology, McGill University, 1977, vol. 4, pp. 161-174.
Terence J Coderre et al., "Contribution of Central Neuroplasticity to Pathological Pain: Review of Clinical and Experimental Evidence", Pain, Review Article, vol. 52, 1993, pp. 259-285.
Louis J Ravin, "Performulation" Pharmaceutics Department, SmithKline Beckman Corporation, pp. 1409-1423, Chapter 76.
Anthony R Disanto, "Bioavailability and Bioequivalency Testing", Clinical Biopharmaceutics/New Formulation Development, The Upjohn Company, pp. 1424-1431, Chapter 77.
Adelbert M Knevel, "Separation", School of Pharmacy and Pharmacal Sciences Purdue University, pp. 1432-1442, Chapter 78.
G Briggs Phillips, "Sterilization", Health Industries manufacturers Association, pp. 1443-1454, Chapter 79.
Frederick P Siegel, "Tonicity, Osmoticity, Osmolality and Osmolarity", College of Pharmacy, University of Illinois, pp. 1455-1472, Chapter 80.
Robert L. Giles, et al., "Plastic Packaging Materials", Glenn Beall Engineering, Inc. et al, pp. 1473-1477, Chapter 81.
Carl J. Lintner, "Stability of Pharmaceutical Products", Lintner Associates, pp. 1478-1486, Chapter 82.
Clyde R Erskine, "Quality Assurance and Control", SmithKline Beckman Corporation, pp. 1487-1491, Chapter 83.
J G Nairn, "Solutions, Emulsions, Suspensions and Extractives", Faculty of Pharmacy, University of Toronto, pp. 1492-1517, Chapter 84.
Kenneth E Avis, "Parenteral Preparations", College of Pharmacy, Universty of Tennessee Center for the Health Sciences, pp. 1518-1541, Chapter 85.
Salvatore J Turco, et al., "Intravenous Admixtures", Temple University School of Pharmacy et al., pp. 1542-1552, Chapter 86.
John D Mullins, "Ophthalmic Preparations", Research and Development Alcon Laboratories, pp. 1553-1566, Chapter 87.
Lawrence H Block, "Medicated Applications", Duquesne University School of Pharmacy, pp. 1567-1584, Chapter 88.
Edward G Ripple, "Powders", College of Pharmacy, University of Minnesota, pp. 1585-1602, Chapter 89.
Robert E King et al., "Oral Solid Dosage Forms", Philadelphia College of Pharmacy and Science, pp. 1603-1632, Chapter 90.
Stuart C Porter, "Coating of Pharmaceutical Dosage Forms", Colorcon, Inc., pp. 1633-1643, Chapter 91.
Mark A Longer et al., "Sustained Release Drug Delivery Systems", School of Pharmacy, University of Wisconsin, pp. 1644-1661, Chapter 92.
John J Sclarra et al., "Aerosols", Arnold & Marie Schwartz College of Pharmacy and Health Sciences, pp. 1662-1677, Chapter 93.
International Search Report dated Oct. 11, 2006 with English translation of relevant portion (Eleven (11) pages).
German Search Report dated Oct. 14, 2005 with English translation of relevant portion (Nine (9) pages).
J. H. Barnes, et. al., *The Preparation and Pharmacology of Some Phenolic Carbamates and Allophanates*, Journal of Pharmacy and Pharmacology, 1961, No. 13, pp. 39-48.
English translation of the International Preliminary Report on Patentability, (one page PCT/IB/338), Jan. 2, 2008.
S. Marinelli et al., The Journal of Neuroscience, vol. 23, Issue 8, pp. 3136-3144 (2003).
Donnerer J., Liebmann I., Schicho R., Pharmacology. Feb. 2005; vol. 73, Issue 2, pp. 97-101 (2005) E pub Oct. 18, 2004.
V. Micale et al., Neurobiology of Disease, Issue 36, pp. 70-80 (2009).
M. Fu et al., Medical Hypotheses vol. 73, pp. 100-102 (2009).

(Continued)

*Primary Examiner* — Fiona T Powers
(74) *Attorney, Agent, or Firm* — Crowell & Moring LLP

(57) ABSTRACT

The present invention relates to salts of substituted allophanates, methods for their production, medicaments containing said compounds and the use of said compound for the production of medicaments.

15 Claims, No Drawings

OTHER PUBLICATIONS

C. Maggi, Life Sciences, vol. 51, No. 23, pp. 1777-1781 (1992).
H. Rami et al., Therapeutic Strategies, vol. 1, Issue 1, pp. 97-104 (2004).
L.A. Birder et al., Nature Neuroscience, vol. 5, No. 9, pp. 856-860 (2002).
P. Holzer, European Journal of Pharmacology vol. 500, pp. 231-241 (2004).
Y. Yiangou et al., The Lancet, vol. 357, p. 1338-1339, Apr. 28, (2001).
P. Geppetti et al., British Journal of Pharmacology, vol. 141, No. 8, pp. 1313-1320 (2004).
W. Huang et al., Journal of Hypertension vol. 27 (2009).
E. Bodo et al., American Journal of Pathology, vol. 166, No. 4, pp. 985-998 (2005).
Won-Sik Shim et al., The Journal of Neuroscience, vol. 27, No. 9, pp. 2331-2337 (2007).
F. Leung, Life Sciences, Issue 83, pp. 1-5 (2008).
A. Suri et al., Trends in Pharmacological Sciences, vol. 29, No. 1, pp. 29-36 (2007).
G. Ahern, The Journal of Biological Chemistry, vol. 278, No. 33, pp. 30429-30434 (2003).
I.-J. You et al., Soc. Neurosci. Abstr. vol. 912.22 (2007).
J. Li et al., Pharmacological Research vol. 57, Issue 3, pp. 239-246 (2008).
H. Schultz, Journal of Physiology, 551.2, p. 400 (2003).
M. Zahner et al., Journal of Physiology 551.2, pp. 515-523 (2003).
H. Pan et al., Circulation Journal of the American Heart Association, Circulation vol. 110, Issue 13, pp. 1826-1831 (2004).
M. Ghasemi et al., European Journal of Pharmacology vol. 544, Issues 1-3, pp. 138-145 (2006).
S. Mandadi et al., Neuroscience vol. 162 pp. 1377-1397 (2009).
D. Dawbarn et al., Neuropharmacology, vol. 20, pp. 341-346 (1981).
R. Marsch et al., The Journal of Neuroscience, vol. 27, No. 4, pp. 832-839 (2007).
H. Eilers, Molecular Interventions, vol. 8, Issue 5, pp. 226-229 (2008).

* cited by examiner

SALTS OF SUBSTITUTED ALLOPHANATES AND THEIR USE IN DRUGS

The present invention relates to salts of substituted allophanates, methods of production thereof, medicaments containing these compounds and the use of said compounds for the production of medicaments.

The treatment of pain, especially of neuropathic pain, is of great importance in medicine. There is a worldwide demand for effective treatments for pain. The urgent need for patient-based, targeted treatment of chronic and non-chronic pain conditions, meaning the successful and satisfactory treatment of pain for the patient, is also evident from the large number of scientific works that have been published recently in the area of applied analgesia and basic research into nociception.

A suitable starting point for the treatment of pain—in particular of pain selected from the group comprising acute pain, chronic pain, neuropathic pain and visceral pain, especially preferably neuropathic pain—is the vanilloid receptor of subtype 1 (VR1/TRPV1), which often is also termed the capsaicin receptor. This receptor is stimulated by, among others, vanilloids such as capsaicin, heat and protons and plays a central role in the development of pain. Furthermore, it is important for numerous other physiological and pathophysiological processes, for example migraine; depression; neurodegenerative diseases; cognitive diseases; anxiety states; epilepsy; cough; diarrhoea; pruritus; disorders of the cardiovascular system; eating disorders; dependence on medicaments; abuse of medicaments and in particular urinary incontinence.

One object of the present invention was therefore to make novel compounds available, which are suitable in particular as pharmacological actives in medicaments, preferably in medicaments for the treatment of disorders or diseases that are mediated at least partially by vanilloid receptors 1 (VR1/TRPV1 receptors).

It was found, surprisingly, that salts of substituted allophanates of the composition stated hereunder are suitable for controlling pain and display excellent affinity for the vanilloid receptor of subtype 1 (VR1/TRPV1 receptor) and are therefore suitable in particular for the prophylaxis and/or treatment of disorders or diseases that are mediated at least partially by vanilloid receptors 1 (VR1/TRPV1).

One object of the present invention therefore comprises salts of substituted allophanates from a cationic salt partner of general formula I,

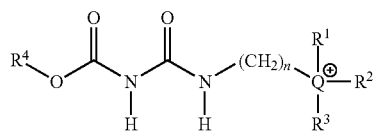

I in which
n=1, 2, 3, 4, 5 or 6;
Q represents a nitrogen atom or a phosphorus atom;
$R^1$, $R^2$, $R^3$ independently of one another, each represent a linear or branched $C_{1-5}$-alkyl residue;
  or two of these residues together with the atom joining them Q as ring member, form a 4-, 5-, 6- or 7-membered, saturated or unsaturated heterocycle, unsubstituted or substituted one or more times, optionally having at least one further heteroatom as ring member and in each case the remaining residue has the meaning stated previously;

$R^4$ represents a linear or branched, saturated or unsaturated aliphatic residue, unsubstituted or substituted one or more times, optionally having at least one heteroatom as a unit of the chain;
  an unsaturated or saturated cycloaliphatic residue, unsubstituted or substituted one or more times, optionally having at least one heteroatom as ring member, which can be joined via a linear or branched alkylene group,
  an aryl residue or heteroaryl residue, unsubstituted or at least substituted one or more times, optionally joined via a linear or branched alkylene group, or
  represents a group $-(CH_2)_q-A_r-(CH_2)_s-B-(CH_2)_t-C_u-R^5$, in which
    q, s and t, independently of one another, each represent 0, 1, 2, 3, 4, 5 or 6;
    r and u, independently of one another, each represent 0 or 1;
    A and C, independently of one another, each represent O, S or NH;
    B represents a linear or branched alkylene, alkenyl or alkinyl group, unsubstituted or substituted one or more times; an unsaturated or saturated cycloaliphatic residue, unsubstituted or substituted one or more times, optionally having at least one heteroatom as ring member; or an aryl residue or heteroaryl residue, unsubstituted or substituted one or more times; and
    $R^5$ represents a linear or branched, saturated or unsaturated aliphatic residue, unsubstituted or substituted one or more times,
in each case optionally in the form of one of its pure stereoisomers, in particular enantiomers or diastereomers, its racemate or in the form of a mixture of stereoisomers, in particular of enantiomers and/or diastereomers, in any proportions, and an anionic salt partner.

If one or both of the substituents $R^4$ and $R^5$ represent a saturated or unsaturated aliphatic residue, i.e. an alkyl, alkenyl or alkinyl residue, this can preferably be substituted with optionally 1, 2, 3, 4, 5, 6, 7, 8 or 9 substituents selected independently of one another from the group comprising F, Cl, Br, I, $-CN$, $-NO_2$, $-OH$, $-NH_2$, $-SH$, $-O(C_{1-5}$-alkyl), $-S(C_{1-5}$-alkyl), $-NH(C_{1-5}$-alkyl), $-N(C_{1-5}$-alkyl)$(C_{1-5}$-alkyl), $-OCF_3$ and $-SCF_3$. Alkenyl residues have at least one, for example 1, 2, 3 or 4, C—C double bonds and alkinyl residues have at least one, for example 1, 2, 3 or 4 C—C triple bonds.

If substituent $R^4$ represents an aliphatic residue that has at least 1, for example 1, 2, 3 or 4 heteroatoms as chain unit(s), these can be selected independently of one another, preferably from the group comprising oxygen, sulphur and nitrogen.

If two of the residues $R^1$, $R^2$ and $R^3$, together with the atom joining them Q as ring member, form a 4-, 5-, 6- or 7-membered, saturated or unsaturated, heterocycle, which is substituted one or more times, for example 1, 2, 3, 4 or 5 times, its substituents can be selected independently of one another from the group comprising oxo (=O), thioxo (=S), F, Cl, Br, I, $-CN$, $-CF_3$, $-SF_5$, $-OH$, $-O-CH_3$, $-O-C_2H_5$, $-O-C(CH_3)_3$, $-NH_2$, $-NO_2$, $-O-CF_3$, $-SCF_3$, $-SH$, $-S-CH_3$, $-S-C_2H_5$, $-S-C(CH_3)_3$, methyl, ethyl, n-propyl, isopropyl, n-butyl, sec-butyl, isobutyl, tert-butyl, n-pentyl, sec-pentyl, $-C(=O)-OH$, $-C(=O)-O-CH_3$, $-C(=O)-O-C_2H_5$, $-N(CH_3)_2$, $-N(C_2H_5)_2$, $-N(H)(CH_3)$, $-N(H)(C_2H_5)$, $-O$-phenyl, $-O$-benzyl, phenyl and benzyl, and in each case the cyclic moiety of the residues $-O$-phenyl, $-O$-benzyl, phenyl and benzyl can be substituted with 1, 2, 3, 4 or 5 substituents selected independently of one another from the group comprising F, Cl, Br, $-OH$, —CF$_3$, —SF$_5$, —CN, —NO$_2$, methyl, ethyl, n-propyl, isopropyl, n-butyl, isobutyl, tert-butyl, —O—CH$_3$, —O—C$_2$H$_5$, —O—C(CH$_3$)$_3$, —O—CF$_3$, —S—CF$_3$, phenyl and —O-benzyl. If the heterocycle formed with Q has one or more, for example 1 or 2, further heteroatoms as ring members, these can be selected independently of one another, preferably from the group comprising nitrogen, oxygen and sulphur.

If one or both of the residues R$^4$ and B represent an unsaturated or saturated cycloaliphatic residue, optionally having at least one heteroatom as ring member or have such a residue that is substituted one or more times, for example 1, 2, 3, 4 or 5 times, its substituents can be selected independently of one another from the group comprising oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —SCF$_3$, —SH, —S—CH$_3$, —S—C$_2$H$_5$, —S—C(CH$_3$)$_3$, methyl, ethyl, n-propyl, isopropyl, n-butyl, sec-butyl, isobutyl, tert-butyl, n-pentyl, sec-pentyl, —C(=O)—OH, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —O-phenyl, —O-benzyl, phenyl and benzyl, and in each case the cyclic moiety of the residues —O-phenyl, —O-benzyl, phenyl and benzyl can be substituted with 1, 2, 3, 4 or 5 substituents selected independently of one another from the group comprising F, Cl, Br, —OH, —CF$_3$, —SF$_5$, —CN, —NO$_2$, methyl, ethyl, n-propyl, isopropyl, n-butyl, isobutyl, tert-butyl, —O—CH$_3$, —O—C$_2$H$_5$, —O—C(CH$_3$)$_3$, —O—CF$_3$, —S—CF$_3$, phenyl and —O-benzyl. If this cycloaliphatic residue has one or more, for example 1 or 2, heteroatoms as ring members, these can be selected independently of one another, preferably from the group comprising nitrogen, oxygen and sulphur.

We may mention, as examples, the residues cyclopropyl, cyclobutyl, cyclopentyl, cyclohexyl, cyclohexyl, cyclooctyl, cyclononyl, cyclopentenyl, cyclohexenyl, cycloheptenyl, cyclooctenyl, imidazolinyl, aziridinyl, azetidinyl, pyrrolidinyl, piperidinyl, azepanyl, azokanyl, piperazinyl, tetrahydrofuranyl (tetrahydrofuryl), tetrahydrothienyl (tetrahydrothiophenyl), morpholinyl and thiomorpholinyl.

If one or both of the residues R$^4$ and B represent or have an aryl or heteroaryl residue that is substituted one or more times, for example 1, 2, 3, 4 or 5 times, its substituents can be selected independently of one another from the group comprising F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —SCF$_3$, —SH, —S—CH$_3$, —S—C$_2$H$_5$, —S—C(CH$_3$)$_3$, methyl, ethyl, n-propyl, isopropyl, n-butyl, sec-butyl, isobutyl, tert-butyl, n-pentyl, sec-pentyl, —C(=O)—OH, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —O-phenyl, —O-benzyl, phenyl and benzyl, and in each case the cyclic moiety of the residues —O-phenyl, —O-benzyl, phenyl and benzyl can be substituted with 1, 2, 3, 4 or 5 substituents selected independently of one another from the group comprising F, Cl, Br, —OH, —CF$_3$, —SF$_5$, —CN, —NO$_2$, methyl, ethyl, n-propyl, isopropyl, n-butyl, isobutyl, tert-butyl, —O—CH$_3$, —O—C$_2$H$_5$, —O—C(CH$_3$)$_3$, —O—CF$_3$, —S—CF$_3$, phenyl and —O-benzyl. The heteroaryl residue can have one or more, for example 1, 2 or 3, heteroatoms as ring members, which are selected independently of one another preferably from the group comprising nitrogen, oxygen and sulphur.

Phenyl, 1-naphthyl and 2-naphthyl may be mentioned as examples of aryl residues.

Pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl may be mentioned as examples of heteroaryl residues.

Substituted alkylene, alkenyl or alkinyl groups can be substituted for example with 1, 2 or 3 substituents selected independently of one another from the group comprising F, Cl, Br, OH, —O—C$_{1-3}$-alkyl, SH and S—C$_{1-3}$-alkyl.

Salts according to the invention based on cationic salt partners of the aforementioned general formula I, in which R$^1$, R$^2$, R$^3$, independently of one another, each represent an
  alkyl residue, selected from the group comprising methyl, ethyl, n-propyl and isopropyl,
  or two of these residues, together with the atom joining them Q as ring member, form a 4-, 5-, 6- or 7-membered, saturated or unsaturated heterocycle, unsubstituted or substituted one or more times, optionally having at least one further heteroatom as ring member and in each case the remaining residue represents an alkyl residue that is selected from the group comprising methyl, ethyl, n-propyl and isopropyl,
and in each case Q, n, R$^4$, R$^5$, q, r, s, t, u, A, B and C have the meaning stated previously, are preferred.

Moreover, salts according to the invention based on cationic salt partners of the aforementioned general formula I, in which
R$^4$ represents a linear or branched, saturated or unsaturated, aliphatic C$_{1-30}$ residue, unsubstituted or substituted one or more times;
  an unsaturated or saturated, 5-, 6- or 7-membered cycloaliphatic residue, unsubstituted or substituted one or more times, optionally having one, two or three heteroatoms as ring member, which can be bound via a linear or branched C1-3 alkylene group,
  a 5- or 6-membered aryl residue or heteroaryl residue, unsubstituted or substituted at least once, optionally bound via a linear or branched C$_{1-3}$-alkylene group, or
  a group —(CH$_2$)$_q$-A$_r$-(CH$_2$)$_s$—B—(CH$_2$)$_t$—C$_u$—R$^5$, in which
    q, s and t, independently of one another, each represent 0, 1, 2, 3, 4, 5 or 6;
    r and u, independently of one another, each represent 0 or 1;
    A and C, independently of one another, each represent O or S;
    B represents a linear or branched C$_{1-6}$-alkylene, C$_{2-6}$-alkenyl or C$_{2-6}$-alkinyl group; which can be substituted with 1, 2 or 3 substituents selected independently of one another from the group comprising F, Cl, Br, OH, —O—C$_{1-3}$-alkyl, SH and —S—C$_{1-3}$-alkyl,
    a (hetero)cycloaliphatic residue selected from the group comprising cyclopropyl, cyclobutyl, cyclopentyl, cyclohexyl, cyclohexyl, cyclooctyl, cyclononyl, cyclopentenyl, cyclohexenyl, cycloheptenyl, cyclooctenyl, imidazolinyl, aziridinyl, azetidinyl, pyrrolidinyl, piperidinyl, azepanyl, azokanyl, piperazinyl, tetrahydrofuranyl (tetrahydrofuryl), tetrahydrothienyl (tetrahydrothiophenyl), morpholinyl and thiomorpholinyl,
    or a (hetero)aryl residue selected from the group comprising pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl, and R⁵ represents a linear or branched, saturated or unsaturated, aliphatic $C_{1-30}$ residue, unsubstituted or substituted one or more times, and and in each case $R^1$, $R^2$, $R^3$, Q, n, q, r, s, t, u, A, B and C have the meaning stated previously, are preferred.

Moreover, salts according to the invention based on cationic salt partners of the aforementioned general formula I, in which n=1, 2, 3, 4, 5 or 6;

Q represents N or P;

$R^1$, $R^2$, $R^3$ independently of one another, each represent an alkyl residue that is selected from the group comprising methyl, ethyl, n-propyl and isopropyl, or two of these residues, together with the atom joining them Q as ring member, form a 4-, 5-, 6- or 7-membered, saturated, unsubstituted heterocycle and in each case the remaining residue represents an alkyl residue that is selected from the group comprising methyl, ethyl, n-propyl and isopropyl, $R^4$ represents a linear or branched, saturated or unsaturated aliphatic $C_{1-20}$ residue;

an aryl or heteroaryl residue, optionally bound via a $C_{1-3}$-alkylene group, selected from the group comprising phenyl, naphthyl, furanyl, thiophenyl and pyridinyl, the cyclic moiety of these residues in each case being unsubstituted or can be substituted with 1, 2, 3, 4 or 5 substituents selected from the group comprising F, Cl, Br, linear or branched $C_{1-3}$-alkyl, linear or branched $C_{1-3}$-alkoxy, phenyl, phenoxy, benzyl and benzyloxy;

represents a group —$(CH_2)_q$—$A_r$—$(CH_2)_s$—B—$(CH_2)_t$—$C_u$—$R^5$, in which q, s and t, independently of one another, each represent 0, 1 or 2;

r and u, independently of one another, each represent 0 or 1;

A and C, independently of one another, each represent O;

B represents a linear or branched $C_{1-6}$-alkylene, $C_{2-6}$-alkenyl or $C_{2-6}$-alkinyl group; which can be substituted with 1, 2 or 3 substituents selected independently of one another from the group comprising F, Cl, Br, OH, —O—$C_{1-3}$-alkyl, SH and —S—$C_{1-3}$-alkyl, represents a (hetero)cycloaliphatic residue selected from the group comprising cyclopropyl, cyclobutyl, cyclopentyl, cyclohexyl, cyclohexyl, cyclooctyl, cyclononyl, cyclopentenyl, cyclohexenyl, cycloheptenyl, cyclooctenyl, imidazolinyl, aziridinyl, azetidinyl, pyrrolidinyl, piperidinyl, azepanyl, azokanyl, piperazinyl, tetrahydrofuranyl (tetrahydrofuryl), tetrahydrothienyl (tetrahydrothiophenyl), morpholinyl and thiomorpholinyl, or represents a (hetero)aryl residue selected from the group comprising pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl, and $R^5$ represents a linear or branched, saturated or unsaturated aliphatic $C_{1-20}$ residue, are further preferred.

Moreover, salts according to the invention based on cationic salt partners of general formula Ia

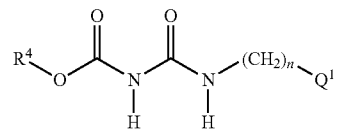

in which n represents 1, 2 or 3;

$Q^1$ represents a residue that is selected from the group comprising

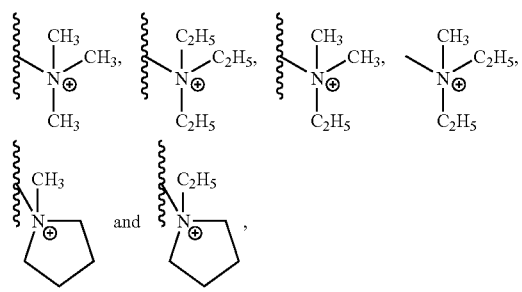

$R^4$ represents a linear or branched $C_{1-20}$ alkyl residue;

a phenyl or benzyl residue, and the cyclic moiety of these residues can be unsubstituted or can be substituted with 1, 2, 3, 4 or 5 substituents selected from the group comprising F, Cl, Br, linear or branched $C_{1-3}$-alkyl, linear or branched $C_{1-3}$-alkoxy, phenyl, phenoxy, benzyl and benzyloxy;

or represents a residue selected from the group comprising

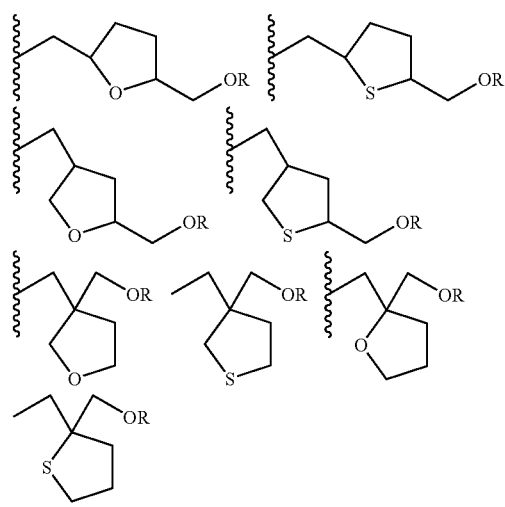

in which R in each case represents a linear or branched $C_{1-20}$-alkyl residue, are further preferred.

Moreover, salts according to the invention based on cationic salt partners of the aforementioned general formula Ia, in which n represents 1, 2 or 3, $Q^1$ represents a residue, which is selected from the group comprising

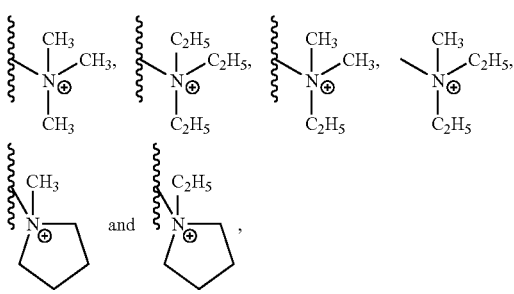

R⁴ represents an alkyl residue selected from the group comprising methyl, ethyl, n-propyl, n-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl and n-eicosanyl;

a phenyl or benzyl residue, and the cyclic moiety of these residues can be unsubstituted or substituted once with a substituent selected from the group comprising F, Cl, Br, linear or branched $C_{1-3}$-alkyl, linear or branched $C_{1-3}$-alkoxy, phenyl, phenoxy, benzyl and benzyloxy;

or represents one of the following residues,

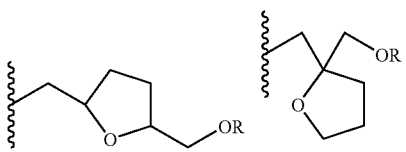

in which R in each case represents an alkyl residue selected from the group comprising methyl, ethyl, n-propyl, n-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl and n-eicosanyl, are further preferred.

Usual salt partners known by a person skilled in the art, in particular pharmaceutically compatible salt partners, can be used as anionic salt partners. Consideration may be given to a halide ion or a hydroxyl ion, especially preferably a chloride, bromide or iodide ion, and quite especially preferably an iodide ion, as anionic salt partner. A given anionic salt partner can also be replaced with another anionic salt partner by ester interchange, by usual methods known by a person skilled in the art.

Salts of substituted allophanates are quite especially preferred that are selected from the group comprising

[1] 4-(Trimethylamino-1-ethyl)allophanic acid dodecyl ester iodide,
[2] 4-(Pyrrolidinium-1-ethyl)allophanic acid hexadecyl ester iodide,
[3] 4-(Trimethylamino-1-propyl)allophanic acid hexadecyl ester iodide,
[4] 4-(Trimethylamino-1-ethyl)allophanic acid octyl ester iodide,
[5] 4-(Trimethylamino-1-ethyl)allophanic acid butyl ester iodide,
[6] 4-(Trimethylamino-1-ethyl)allophanic acid phenyl ester iodide,
[7] 4-Benzyloxycarbonyl-4-(N-methyldimethylammonium-1-ethyl)allophanic acid benzyl ester iodide,
[8] 4-(Trimethylamino-1-ethyl)allophanic acid benzyl ester iodide,
[9] 4-(Trimethylamino-1-ethyl)allophanic acid (4-phenyl)-phenyl ester iodide,
[10] 4-(Trimethylamino-1-ethyl)allophanic acid ethyl ester iodide,
[11] 4-(Trimethylamino-1-ethyl)allophanic acid butyl ester iodide,
[12] 4-(Trimethylamino-1-ethyl)allophanic acid hexyl ester iodide,
[13] 4-(Trimethylamino-1-ethyl)allophanic acid (cis-5-hexadecyloxymethyltetrahydrofuran-2-yl)methyl ester iodide,
[14] 4-(Trimethylamino-1-ethyl)allophanic acid 3-hexadecyloxy-2-methoxypropan-1-yl ester iodide,
[15] 4-(Trimethylamino-1-ethyl)allophanic acid hexadecyl ester iodide and
[16] 4-(Trimethylamino-1-ethyl)allophanic acid (2-hexadecyloxymethyltetrahydrofuran-2-yl)methyl ester iodide.

Salts according to the invention may also be preferred that display, in the FLIPR Assay at a concentration of 10 µM, an inhibition of $Ca^{2+}$ ion influx in rat dorsal root ganglia of at least 10%, preferably at least 30%, especially preferably at least 50%, quite especially preferably at least 70%, even more preferably at least 90%, in comparison with the maximum achievable inhibition of $Ca^{2+}$ ion influx with capsaicin at a concentration of 10 µM.

In the FLIPR Assay the $Ca^{2+}$ influx is quantified by means of a $Ca^{2+}$-sensitive dye (Type Fluo-4, Molecular Probes Europe BV, Leyden, The Netherlands) in the Fluorescent Imaging Plate Reader (FLIPR, Molecular Devices, Sunnyvale, USA), as described below.

Another object of the present invention is a method of production of the salts of substituted allophanates according to the invention, according to which a compound of general formula II,

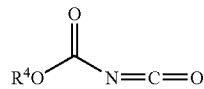

II in which R⁴ has the meaning stated previously, is reacted in an optionally absolute reaction medium, preferably in diethyl ether, at low temperatures, preferably −15 to +5° C.; optionally in the presence of a base, preferably an organic amine such as triethylamine for example, with a compound of general formula III

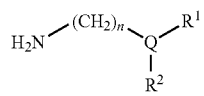

III in which n, R¹ and R² have the meaning stated previously, to a compound of general formula III,

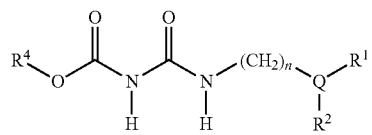

III or a corresponding salt of acid addition, for example the hydrochloride, where R¹, R², R⁴ and n have the meaning stated previously, and the compound of general formula III thus obtained is converted by reaction in an optionally absolute reaction medium such as dimethylformamide or tetrahydrofuran, optionally in the presence of a base such as diisopropylethylamine, with an alkylating agent, preferably a $C_{1, 2, 3, 4 \text{ or } 5}$-alkyl iodide, to a compound of general formula I and this is optionally purified and isolated.

The chemicals and reactants used are commercially available or can be produced by usual methods known by a person skilled in the art. For example, the compounds of general formula II can be obtained according to the following scheme 1:

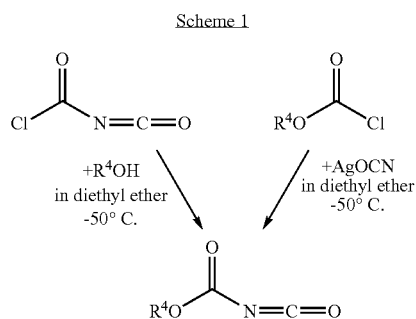

The reactions described above can moreover be carried out in each case in usual conditions that are familiar to a person skilled in the art, for example with respect to pressure, temperature, protective gas atmosphere or order of adding the components. If necessary, the procedure that is the optimum in particular conditions can be determined by a person skilled in the art by means of simple preliminary experiments.

The intermediates and end products obtained by the reactions described above can in each case, if desired and/or necessary, be purified and/or isolated by usual methods, known by a person skilled in the art. Suitable methods of purification are for example extraction methods and chromatographic methods such as column chromatography or preparative chromatography.

All of the process steps described above and in each case also the purification and/or isolation of intermediates or end products can advantageously be carried out partially or completely under an inert gas atmosphere, preferably under a nitrogen atmosphere or argon atmosphere.

The salts of substituted allophanates according to the invention are toxicologically harmless and are therefore suitable as pharmaceutical actives in medicaments.

The present invention therefore further relates to medicaments containing at least one salt of a substituted allophanate according to the invention and optionally one or more pharmaceutically compatible excipients.

Said medicaments according to the invention are suitable in particular for vanilloid receptor 1 (VR1/TRPV1) regulation, preferably for vanilloid receptor 1 (VR1/TRPV1) inhibition and/or for vanilloid receptor 1 (VR1/TRPV1) stimulation.

Preferably the medicaments according to the invention are also suitable for the prophylaxis and/or treatment of disorders or diseases that are mediated at least partially by vanilloid receptors 1.

Preferably the medicament according to the invention is suitable for the treatment and/or prophylaxis of one or more diseases selected from the group comprising pain, preferably of pain selected from the group comprising acute pain, chronic pain, neuropathic pain and visceral pain; arthralgia; migraine; depression; nervous complaints; nerve damage; neurodegenerative diseases, preferably selected from the group comprising multiple sclerosis, Alzheimer's disease, Parkinson's disease and Huntington's disease; cognitive dysfunctions, preferably cognitive impairment, especially preferably memory disorders; epilepsy; respiratory tract diseases, preferably selected from the group comprising asthma and pneumonia; cough; urinary incontinence; overactive bladder (OAB); gastric ulcers; irritable bowel syndrome; cerebrovascular accidents; eye irritations; skin irritations; neurotic skin diseases; inflammatory diseases, preferably intestinal inflammations; diarrhoea; pruritus; eating disorders, preferably selected from the group comprising bulimia, cachexia, anorexia and obesity; dependence on medicaments; abuse of medicaments; withdrawal effects in dependence on medicaments; development of tolerance to medicinal drugs, preferably to natural or synthetic opioids; drug dependence; drug abuse; withdrawal effects in drug dependence; alcohol dependence; alcohol abuse and withdrawal effects in alcohol dependence; for diuresis; for antinatriuresis; for exerting an influence on the cardiovascular system; for increasing alertness; for increasing libido; for modulation of motor activity; for anxiety reduction; for local anaesthesia and/or for suppression of undesirable side effects, preferably selected from the group comprising hyperthermia, hypertension and bronchial constriction, induced by the administration of vanilloid receptor 1 (VR1/TRPV1 receptors) agonists, preferably selected from the group comprising capsaicin, resiniferatoxin, olvanil, arvanil, SDZ-249665, SDZ-249482, nuvanil and capsavanil.

Especially preferably, the medicament according to the invention is suitable for the treatment and/or prophylaxis of one or more diseases selected from the group comprising pain, preferably of pain selected from the group comprising acute pain, chronic pain, neuropathic pain and visceral pain; migraine; depression; neurodegenerative diseases, preferably selected from the group comprising multiple sclerosis, Alzheimer's disease, Parkinson's disease and Huntington's disease; cognitive dysfunctions, preferably cognitive impairment, especially preferably memory disorders; urinary incontinence; overactive bladder (OAB); dependence on medicaments; abuse of medicaments; withdrawal effects in dependence on medicaments; development of tolerance to medicinal drugs, preferably development of tolerance to natural or synthetic opioids; drug dependence; drug abuse; withdrawal effects in drug dependence; alcohol dependence; alcohol abuse and withdrawal effects in alcohol dependence.

Quite especially preferably, the medicament according to the invention is suitable for the treatment and/or prophylaxis of pain, preferably of pain selected from the group comprising acute pain, chronic pain, neuropathic pain and visceral pain, and/or urinary incontinence.

Another object of the present invention is the use of at least one salt of a substituted allophanate according to the invention, and optionally of one or more pharmaceutically compatible excipients for the production of a medicament for vanilloid receptor 1 (VR1/TRPV1) regulation, preferably for vanilloid receptor 1 (VR1/TRPV1) inhibition and/or for vanilloid receptor 1 (VR1/TRPV1) stimulation.

The use of at least one salt of a substituted allophanate according to the invention, and optionally of one or more pharmaceutically compatible excipients, is preferred for the production of a medicament for the prophylaxis and/or treatment of disorders or diseases that are mediated at least partially by vanilloid receptors 1.

The use of at least one salt of a substituted allophanate according to the invention, and optionally of one or more pharmaceutically compatible excipients, is especially preferred for the production of a medicament for the treatment and/or prophylaxis of one or more diseases selected from the group comprising pain, preferably of pain selected from the group comprising acute pain, chronic pain, neuropathic pain and visceral pain; arthralgia; migraine; depression; nervous complaints; nerve damage; neurodegenerative diseases, preferably selected from the group comprising multiple sclerosis, Alzheimer's disease, Parkinson's disease and Huntington's disease; cognitive dysfunctions, preferably cognitive impairment, especially preferably memory disorders; epilepsy; respiratory tract diseases, preferably selected from the group comprising asthma and pneumonia; cough; urinary incontinence; overactive bladder (OAB); gastric ulcers; irritable bowel syndrome; cerebrovascular accidents; eye irritations; skin irritations; neurotic skin diseases; inflammatory diseases, preferably intestinal inflammations; diarrhoea; pruritus; eating disorders, preferably selected from the group comprising bulimia, cachexia, anorexia and obesity; dependence on medicaments; abuse of medicaments; withdrawal effects in dependence on medicaments; development of tolerance to medicinal drugs, preferably to natural or synthetic opioids; drug dependence; drug abuse; withdrawal effects in drug dependence; alcohol dependence; alcohol abuse and withdrawal effects in alcohol dependence; for diuresis; for antinatriuresis; for exerting an influence on the cardiovascular system; for increasing alertness; for increasing libido; for modulation of motor activity; for anxiety reduction; for local anaesthesia and/or for suppression of undesirable side effects, preferably selected from the group comprising hyperthermia, hypertension and bronchial constriction, induced by the administration of vanilloid receptor 1 (VR1/TRPV1 receptor) agonists, preferably selected from the group comprising capsaicin, resiniferatoxin, olvanil, arvanil, SDZ-249665, SDZ-249482, nuvanil and capsavanil.

The use of at least one salt of a substituted allophanate according to the invention and optionally of one or more pharmaceutically compatible excipients, is quite especially preferred for the production of a medicament for the treatment and/or prophylaxis of one or more diseases selected from the group comprising pain, preferably of pain selected from the group comprising acute pain, chronic pain, neuropathic pain and visceral pain; migraine; depression; neurodegenerative diseases, preferably selected from the group comprising multiple sclerosis, Alzheimer's disease, Parkinson's disease and Huntington's disease; cognitive dysfunctions, preferably cognitive impairment, especially preferably memory disorders; urinary incontinence; overactive bladder (OAB); dependence on medicaments; abuse of medicaments; withdrawal effects in dependence on medicaments; development of tolerance to medicinal drugs, preferably development of tolerance to natural or synthetic opioids; drug dependence; drug abuse; withdrawal effects in drug dependence; alcohol dependence; alcohol abuse and withdrawal effects in alcohol dependence.

The use of at least one salt of a substituted allophanate according to the invention and optionally of one or more pharmaceutically compatible excipients, is even more preferred for the production of a medicament for the treatment and/or prophylaxis of pain, preferably selected from the group comprising acute pain, chronic pain, neuropathic pain and visceral pain, and/or urinary incontinence.

The medicament according to the invention is suitable for administration to adults and children including young children and infants.

The medicament according to the invention can be a liquid, semi-solid or solid pharmaceutical form, for example in the form of solutions for injection, drops, juices, syrups, sprays, suspensions, tablets, patches, capsules, plasters, suppositories, ointments, creams, lotions, gels, emulsions, aerosols or in multiparticulate form, for example in the form of pellets or granules, optionally compressed into tablets, filled in capsules or suspended in a liquid, and can also be administered as such. In addition to at least one salt according to the invention, the medicament according to the invention usually contains other physiologically compatible pharmaceutical excipients, which can preferably be selected from the group comprising vehicles, fillers, solvents, diluents, surfactants, colorants, preservatives, disintegrants, glidants, lubricants, flavours and binders.

The choice of physiologically compatible excipients and the amounts of them to be used depends on whether the medicament is intended for oral, subcutaneous, parenteral, intravenous, intraperitoneal, intradermal, intramuscular, intranasal, buccal, rectal or local application, for example for infections on the skin, the mucous membranes and the eyes. Preferably preparations in the form of tablets, coated tablets, capsules, granules, pellets, drops, juices and syrups are suitable for oral application, and solutions, suspensions, easily reconstituted dry preparations and sprays for parenteral, topical and inhalation application.

The salts used in the medicaments according to the invention can be in the form of preparations suitable for percutaneous application, in a deposit, in dissolved form or in a plaster, optionally with addition of agents that promote skin penetration.

Pharmaceutical forms for oral or percutaneous application can also provide delayed release of the particular salt according to the invention.

The medicaments according to the invention are manufactured by means of the usual means, devices, methods and processes known from the state of the art, as described for example in "Remingtons Pharmaceutical Sciences", editor A. R. Gennaro, 17th edition, Mack Publishing Company, Easton, Pa., 1985, in particular in Part 8, Sections 76 to 93. The corresponding description is incorporated hereby as reference and is to be regarded as part of the disclosure.

The amount of the particular salt according to the invention that is to be administered to the patient can vary and depends for example on the patient's weight or age and on the method of administration, the indication and the severity of the disease. Usually 0.005 to 100 mg/kg, preferably 0.05 to 75 mg/kg body weight of the patient, of at least one said compound according to the invention, is applied.

Pharmacological Methods:
1. Functional Investigation at the Vanilloid Receptor I (VR1/TRPV1 Receptor)

The agonistic and/or antagonistic action of the test substances at the vanilloid receptor 1 (VR1/TRPV1) of the species rat can be determined with the following assay. According to this assay, the $Ca^{2+}$ influx through the receptor channel is quantified by means of a $Ca^{2+}$-sensitive dye (Type Fluo-4, Molecular Probes Europe BV, Leyden, The Netherlands) in the Fluorescent Imaging Plate Reader (FLIPR, Molecular Devices, Sunnyvale, USA).

Method:
Complete Medium: 50 mL HAMS F12 Nutrient Mixture (Gibco Invitrogen GmbH, Karlsruhe, Germany) with
10 vol. % FCS (fetal calf serum, Gibco Invitrogen GmbH, Karlsruhe, Germany, heat-inactivated);

2 mM L-glutamine (Sigma, Munich, Germany);
1 wt. % AA solution (solution of antibiotics/antimycotics, PAA, Pasching, Austria) and 25 ng/ml medium NGF (2.5 S, Gibco Invitrogen GmbH, Karlsruhe, Germany)

Cell culture plate: poly-D-lysine-coated, black 96-well plates with clear bottom (96-well black/clear plate, BD Biosciences, Heidelberg, Germany) are additionally coated with laminin (Gibco Invitrogen GmbH, Karlsruhe, Germany), diluting laminin to a concentration of 100 µg/mL with PBS (Ca—Mg-free PBS, Gibco Invitrogen GmbH, Karlsruhe, Germany). Aliquots are taken with a laminin concentration of 100 µg/mL and are stored at −20° C. The aliquots are diluted with PBS in the ratio 1:10 to 10 µg/mL laminin and in each case 50 µL of the solution is pipetted into a well of the cell culture plate. The cell culture plates are incubated at 37° C. for at least two hours, the supernatant is drawn off by suction and the wells are each washed twice with PBS. The coated cell culture plates are stored with the supernatant PBS, which is only removed just before loading of the cells.

Preparation of the Cells:

The spinal column is removed from decapitated rats and is placed directly in cold HBSS buffer (on an ice bath) (Hank's buffered saline solution, Gibco Invitrogen GmbH, Karlsruhe, Germany) to which 1 vol. % (percent by volume) of AA solution (antibiotics/antimycotics solution, PAA, Pasching, Austria) has been added. The spinal column is transected longitudinally and is removed together with fasciae from the spinal canal. Then the dorsal root ganglia (DRGs) are removed and stored again in cold HBSS buffer to which 1 vol. % of AA solution has been added. The DRGs, from which all blood residues and spinal nerves have been removed completely, are each transferred to 500 µL of cold collagenase type 2 (PAA, Pasching, Austria) and incubated at 37° C. for 35 minutes. After adding 2.5 vol. % trypsin (PAA, Pasching, Austria) they are incubated at 37° C. for a further 10 minutes. At the end of incubation the enzyme solution is carefully removed by pipette and 500 µL Complete Medium is added to each of the DRGs.

The DRGs are in each case suspended several times, drawn through No. 1, No. 12 and No. 16 needles using a syringe, and transferred to a 50 mL Falcon tube and this is filled with Complete Medium to 15 mL. The contents of each Falcon tube is in each case filtered through a 70 µm Falcon filter insert and centrifuged for 10 minutes at 1200 revolutions, at room temperature. The resultant pellet is in each case taken up in 250 µL Complete Medium and the cell count is determined.

The number of cells in the suspension is adjusted to $3\times10^5$ per mL and in each case 150 µL of this suspension is put in a well of the coated cell culture plates as described previously. The plates are kept in the incubator at 37° C., 5 vol. % $CO_2$ and 95% relative humidity for two to three days.

Then the cells are loaded with 2 µM Fluo-4 and 0.01 vol. % Pluronic F127 (Molecular Probes Europe BV, Leyden, The Netherlands) in HBSS buffer (Hank's buffered saline solution, Gibco Invitrogen GmbH, Karlsruhe, Germany) for 30 min at 37° C., washed 3× with HBSS buffer and, after further incubation of 15 minutes at room temperature, used for $Ca^{2+}$ measurement in the FLIPR Assay. The $Ca^{2+}$-dependent fluorescence is measured before and after adding substances ($\lambda_{ex}$=488 nm, $\lambda_{em}$=540 nm). Quantification is based on measurement of the maximum fluorescence intensity (FC, fluorescence counts) over time.

FLIPR Assay:

The FLIPR protocol comprises 2 additions of the substance. First the test compounds (10 µM) are pipetted onto the cells and the $Ca^{2+}$ influx is compared with the control (capsaicin 10 µM). The result is obtained as % activation relative to the $Ca^{2+}$ signal after adding 10 µM capsaicin (CP). After incubation for 5 minutes, 100 nM capsaicin is applied and the influx of $Ca^{2+}$ is determined again.

Desensitizing agonists and antagonists lead to suppression of $Ca^{2+}$ influx. The % inhibition is calculated compared to the maximum inhibition attainable with 10 µM capsaicin.

Determinations are performed in triplicate (n=3) and are repeated in at least 3 independent experiments (N=4).

Based on the percentage suppression by different concentrations of the test compounds of general formula I, $IC_{50}$ inhibitory concentrations are calculated, which cause 50-percent suppression of capsaicin.

II. Functional Investigation at the Vanilloid Receptor (VR1)

The agonistic and/or antagonistic effects of the test substances on the vanilloid receptor (VR1) can be determined with the following assay. According to this assay the $Ca^{2+}$ influx through the channel is quantified by means of a $Ca^{2+}$-sensitive dye (Type Fluo-4, Molecular Probes, Europe BV, Leyden, The Netherlands) in the Fluorescent Imaging Plate Reader (FLIPR, Molecular Devices, Sunnyvale, USA).

Method:

Chinese hamster ovary cells (CHO K1-cells, European Collection of Cell Cultures (ECACC) Great Britain) are stably transfected with the VR1 gene. For functional studies, these cells are plated on poly-D-lysine-coated, black 96-well plates with clear bottom (BD Biosciences, Heidelberg, Germany) at a density of 25 000 cells/well. The cells are incubated overnight at 37° C. and 5% $CO_2$ in a culture medium (Nutrient Mixture Ham's F12, 10 vol. % FCS (fetal calf serum), 18 µg/ml L-proline). On the next day the cells are incubated for 30 minutes at 37° C. with Fluo-4 (Fluo-4 2 µM, Pluronic F127 0.01 vol. %, Molecular Probes) in HBSS (Hank's buffered saline solution), (Gibco Invitrogen GmbH, Karlsruhe, Germany). Then the plates are washed 3 times with HBSS buffer and, after further incubation of 15 minutes at room temperature, they are used for $Ca^{2+}$ measurement in the FLIPR. The $Ca^{2+}$-dependent fluorescence is measured before and after adding the test substances (wavelength $\lambda_{ex}$=488 nm, $\lambda_{em}$=540 nm). Quantification is based on measurement of the maximum fluorescence intensity (FC, fluorescence counts) over time.

FLIPR Assay:

The FLIPR protocol comprises 2 additions of the substance. First the test substances (10 µM) are pipetted onto the cells and the $Ca^{2+}$ influx is compared with the control (capsaicin 10 µM) (% activation relative to the $Ca^{2+}$ signal after adding 10 µM capsaicin). After incubation for 5 minutes, 100 nM capsaicin is applied and the influx of $Ca^{2+}$ is determined again.

Desensitizing agonists and antagonists led to suppression of $Ca^{2+}$ influx. The % inhibition is calculated compared to the maximum inhibition attainable with 10 µM capsazepin.

III. Formalin Test on the Mouse

The investigation for determination of the antinociceptive action of the salts according to the invention is carried out in the formalin test on male mice (NMRI, 20 to 30 g body weight, Iffa, Credo, Belgium).

In the formalin test, according to D. Dubuisson et al., Pain 1977, 4, 161-174, a distinction is made between the first (early) phase (0 to 15 minutes after formalin injection) and the second (late) phase (15 to 60 minutes after formalin injection). The early phase, as direct reaction to formalin injection, provides a model for acute pain, whereas the late phase is regarded as a model for persistent (chronic) pain (T. J. Coderre et al., Pain 1993, 52, 259-285). The corresponding descriptions in the literature are incorporated hereby as reference and are form part of the disclosure.

The salts according to the invention are investigated in the second phase of the formalin test, to obtain data on the effects of the substances on chronic/inflammatory pain.

The time of application of the salts according to the invention before the formalin injection is selected according to the method of administration of the compounds according to the invention. Intravenous application of 10 mg/kg body weight of the test substances takes place 5 minutes before the formalin injection. This is performed as a single subcutaneous formalin injection (20 μL, 1% aqueous solution) in the dorsal side of the right hindpaw, so that a nociceptive reaction is induced in test animals that can move freely, and is expressed as definite licking and biting of the affected paw.

Then for a period of investigation of three minutes in the second (late) phase of the formalin test (21 to 24 minutes after formalin injection) the nociceptive behaviour is monitored continuously by observing the animals. The pain behaviour is quantified by summation of the seconds during which the animals display licking and biting of the affected paw in the test period.

Comparison is based in each case on control animals that receive the vehicle (0.9% aqueous sodium chloride solution) instead of the compounds according to the invention, before applying formalin.

Based on the quantification of the pain behaviour, the effect of the substance in the formalin test is determined as the change versus the corresponding control, in percent.

After injection of substances that have antinociceptive action in the formalin test, the behavioural reactions of the animals that were described, i.e. licking and biting, are reduced or eliminated.

The present invention is explained in the following on the basis of examples. These explanations are only illustrative and do not limit the general scope of the invention.

EXAMPLES

Synthesis of Salts of Substituted Allophanates

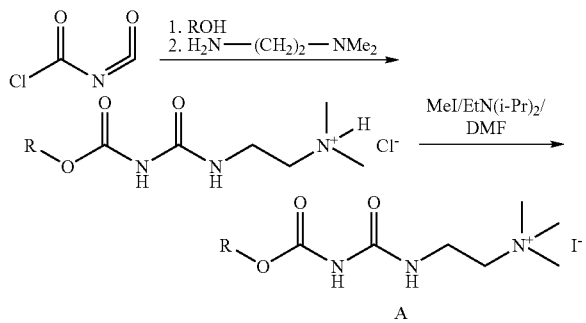

General Specification (1) for the Synthesis of Allophanate Hydrochlorides

A solution of the corresponding alcohol ROH (9.5 mmol) in absolute diethyl ether (50 mL) was slowly added dropwise to a solution of chlorocarbonyl isocyanate (0.76 mL, 9.5 mmol) in absolute diethyl ether (50 mL) at −50° C. under argon. The reaction solution was stirred for 1 hour (h) at −50° C. and then its temperature was raised to 0° C. within one hour. A solution of N,N-dimethylethylenediamine (9.5 mmol) and triethylamine (1 mL) in absolute diethyl ether (50 mL) was then slowly added dropwise to the reaction mixture at 0° C. The reaction mixture was stirred for 16 h at room temperature, acidified with hydrogen chloride in diethyl ether and stirred for 1 h at room temperature. The resultant solid was filtered off, washed with diethyl ether and dried under vacuum. The white solid was suspended in water. The suspension was distributed into two centrifuge tubes, centrifuged 2×20 min at 5000 rev/min and the supernatant was then decanted off. The amorphous solid isolated was dried over phosphorus pentoxide, under vacuum.

4-(N,N-Dimethyl-3-aminoethyl)allophanic acid octyl ester hydrochloride (OG-345.3)

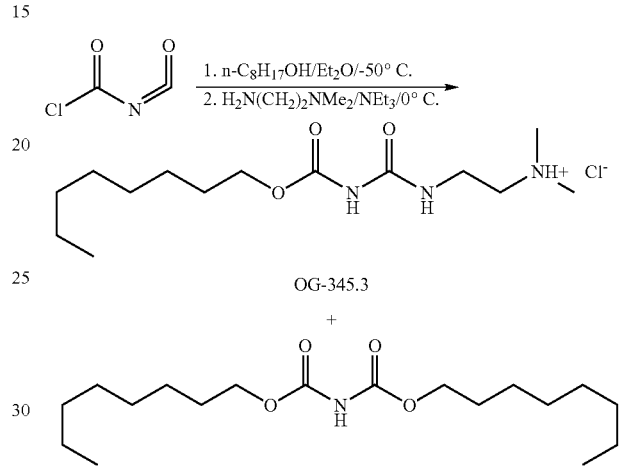

The synthesis was carried out according to general specification (1).

Batch size: chlorocarbonyl isocyanate (0.76 mL, 9.5 mmol); 1-octanol (1.53 mL, 9.5 mmol), N,N-dimethylethylenediamine (1.05 mL, 840 mg, 9.5 mmol), triethylamine (1 mL) in diethyl ether (120 mL)

Yield: 940 mg (31%), white solid

Melting point: 86-92° C.

$^1$H-NMR (DMSO-$d_6$): 0.86 (3 H, t, J=6.8 Hz); 1.20-1.35 (10 H, m); 1.57 (2 H, ddd, J=6.8+6.8+13.7 Hz); 2.58 (6 H, s); 2.92 (2 H, t, J=5.9 Hz); 3.43 (2 H, dd, J=5.9+11.7 Hz); 4.05 (2 H, t, J=6.8 Hz); 7.96 (1 H, t, J=5.9 Hz); 10.00 (1 H, s).

$^{13}$C-NMR (DMSO-$d_6$): 13.94; 22.04; 25.15; 28.18; 28.53 (2 C); 31.13; 35.12; 43.04 (2 C); 56.35; 64.95; 152.79; 153.98.

4-(N,N-Dimethyl-3-aminoethyl)allophanic acid dodecyl ester hydrochloride (OG-350)

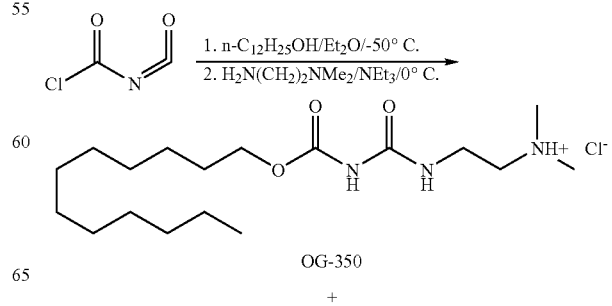

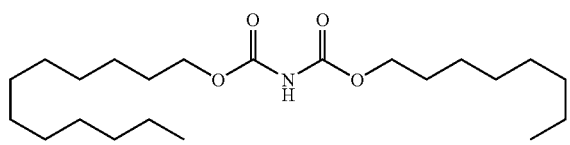

The synthesis was carried out according to general specification (1).

Batch size: chlorocarbonyl isocyanate (0.76 mL, 9.5 mmol), 1-dodecanol (2.2 mL, 9.5 mmol); N,N-dimethylethylenediamine (1.05 mL, 840 mg, 9.5 mmol), triethylamine (1 mL) in diethyl ether (120 mL).

Yield: 410 mg (13%), white solid

Melting point: 115-117° C.

$^1$H-NMR (DMSO-$d_6$): 0.80-0.90 (3 H, m); 1.16-1.36 (18 H, m); 1.50-1.64 (2 H, m); 2.77 (6 H, s); 3.17 (2 H, t, J=5.5 Hz); 3.51 (2 H, dd, J=6.3+11.7 Hz); 4.00-4.10 (2 H, m); 8.01 (1 H, t, J=6.6 Hz); 10.07 (1 H, s).

$^{13}$C-NMR (DMSO-$d_6$): 13.94; 22.06; 25.15; 28.18; 28.58; 28.66; 28.91 (2 C); 28.97 (2 C); 31.25; 34.47; 42.36 (2 C); 55.94; 64.99; 153.02; 153.95.

General Synthesis Specification for the Quarternization of Allophanate Hydrochlorides (V2):

Methyl iodide (310 μL, 710 mg, 5 mmol) was added to a mixture of allophanate hydrochloride (1 mmol) in absolute N,N-dimethylformamide (20 mL) and ethyl diisopropylamine (340 μL, 260 mg, 2 mmol) and then stirred for 2.5 h at 50° C. The reaction mixture was evaporated to dryness under vacuum, the residue was taken up in dichloromethane, concentrated again and then dried under vacuum. Water (80 mL) was added to the residue, and stirred. The resultant suspension was centrifuged (20 min at 5000 rev/min) and then the supernatant was decanted off. The amorphous solid isolated was dried over phosphorus pentoxide, under vacuum.

Example 1

4-(N,N,N-Trimethyl-3-ammonio-ethyl)allophanic acid dodecyl ester iodide (OG-351)

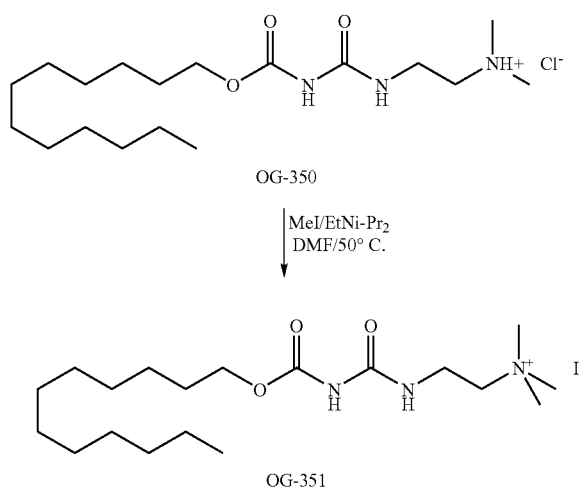

The synthesis was carried out according to general specification (V2).

Batch size: OG-350 (330 mg, 0.87 mmol), ethyl diisopropylamine (306 μL, 233 mg, 1.8 mmol) and methyl iodide (270 μL, 620 mg, 4.4 mmol) in N,N-dimethylformamide (20 mL).

Yield: 410 mg (96%), white solid

Melting point: 138-146° C.

$^1$H-NMR (DMSO-$d_6$): 0.86 (3 H, t, J=6.3 Hz); 1.10-1.36 (18 H, m); 1.50-1.64 (2 H, m); 3.10 (9 H, s); 3.42 (2 H, t, J=6.3 Hz); 3.58-3.64 (2 H, m); 4.06 (2 H, t, J=6.3 Hz); 8.09 (1 H, t, J=6.3 Hz); 10.13 (1 H, s).

$^{13}$C-NMR (DMSO-$d_6$): 13.93; 22.05; 25.12; 28.14; 28.55; 28.64; 28.89 (2 C); 28.95 (2 C); 31.22; 33.72; 52.48; 64.02; 65.06; 152.79; 154.05.

Example 2

Stage 1

4-(Pyrrolidyl-1-ethyl)allophanic acid hexadecyl ester hydrochloride (OG-358)

The synthesis was carried out according to general specification (V1):

Batch size: chlorocarbonyl isocyanate (0.76 mL, 9.5 mmol), 1-hexadecanol (2.30 g, 9.5 mmol), 2-pyrrolidin-1-yl-ethylamine (1.10 g, 9.5 mmol) and triethylamine (1 mL) in diethyl ether (150 mL).

Yield: 580 mg (14%), white solid

Melting point: 105-108° C.

$^1$H-NMR (DMSO-$d_6$+CDCl$_3$): 0.84 (3 H, t, J=7.0 Hz); 1.13-1.35 (26 H, m); 1.58 (2 H, ddd, J=7.0+14.1+14.1 Hz); 1.80-2.10 (4 H, m); 3.0 (1 H, br. s); 3.08 (2 H, dd, J=7.0+14.1 Hz); 3.20-3.40 (2 H, m); 3.52 (2 H, dd, J=6.3+11.7 Hz); 3.59 (1 H, br. s); 4.0-4.12 (2 H, m); 8.06 (1 H, t, J=5.8 Hz); 9.99 (1 H, s).

Stage 2

4-(N-Methylpyrrolidinium-1-ethyl)allophanic acid hexadecyl ester iodide (OG-359)

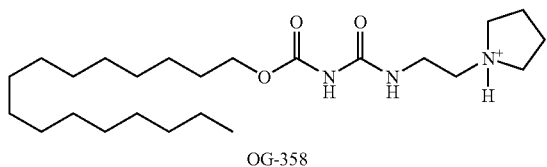

OG-358

| MeI/Et(i-Pr)$_2$
| DMF/50° C.

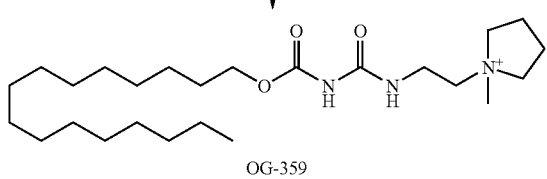

OG-359

The synthesis was carried out according to general specification (V2):

Batch size: OG-358 (480 mg, 1 mmol), ethyl diisopropylamine (340 μL, 260 mg, 2 mmol) and methyl iodide (310 μL, 710 mg, 5 mmol) in N,N-dimethylformamide (20 mL).

Yield: 530 mg (93%), white solid

Melting point: 107-110° C.

$^1$H-NMR (DMSO-d$_6$+CDCl$_3$): 0.85 (3 H, t, J=7.2 Hz); 1.14-1.40 (26 H, m); 1.50-1.63 (2 H, m); 2.92 (4 H, br. s); 3.05 (3 H, s); 3.42-3.67 (8 H, m); 4.06 (2 H, t, J=5.5 Hz); 8.10 (1H, t, J=5.8 Hz); 10.09 (1 H, s).

$^{13}$C-NMR (DMSO-d$_6$+CDCl$_3$): 13.85; 20.91 (2 C); 22.02; 25.10; 28.13; 28.55; 28.61; 28.88; 28.95; 31.20; 34.20; 47.44; 61.69; 63.70 (2 C); 64.98; 152.78; 153.95.

Example 3

Stage 1

4-(N,N-Dimethyl-3-aminopropyl)allophanic acid hexadecyl ester hydrochloride (OG-361)

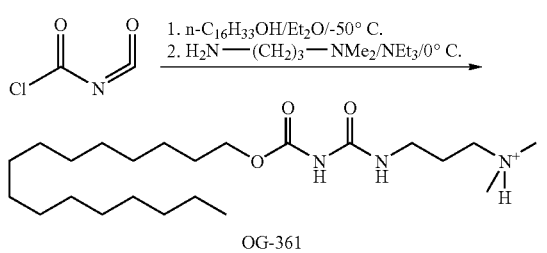

OG-361
+
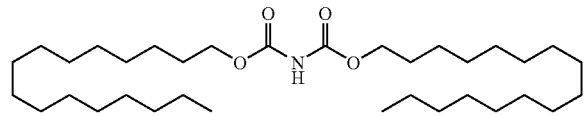

The synthesis was carried out according to general specification (V1).

Batch size: chlorocarbonyl isocyanate (0.76 mL, 9.5 mmol), 1-hexadecanol (2.30 g, 9.5 mmol), N$^1$.N$^1$-dimethylpropane-1,3-diamine (1.2 mL, 970 mg, 9.5 mmol) and triethylamine (1 mL) in diethyl ether (150 mL).

Yield: 1.70 g (40%), white solid

Melting point: 120-123° C.

$^1$H-NMR (CDCl$_3$): 0.85 (3 H, t, J=7.04 Hz); 1.20-1.30 (26 H, m); 1.62 (2 H, ddd, J=7.0+7.0+14.1 Hz); 2.02-2.12 (2 H, m); 2.85 (6 H, s); 3.10-3.16 (2 H, m); 3.38 (2 H, dd, J=6.3+12.5 Hz); 4.09 (2 H, t, J=7.0 Hz); 7.93 (1 H, s); 7.98 (1 H, t, J=6.3 Hz).

Stage 2

4-(N,N,N-Trimethyl-3-ammonio-propyl)allophanic acid hexadecyl ester iodide (OG-362)

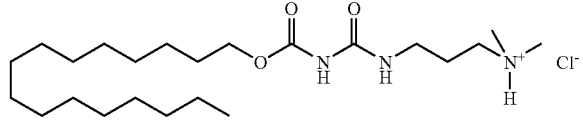

OG-361

| MeI/Et(i-Pr)$_2$
| DMF/50° C.

OG-362

The synthesis was carried out according to general specification V2.

Batch size: OG-361 (450 mg, 1 mmol), ethyl diisopropylamine (340 μL, 260 mg, 2 mmol) and methyl iodide (310 μL, 710 mg, 5 mmol) in N,N-dimethylformamide (20 mL).

Yield: 530 mg (95%), white solid

Melting point: 153-154° C. (transformation of the crystal form at 115-116° C.).

$^1$H-NMR (DMSO-d$_6$): 0.80-0.90 (3 H, m); 1.16-1.40 (26 H. m); 1.57 (2 H, ddd, J=6.8+6.8+13.7 Hz); 1.85-1.94 (2 H, m); 3.05 (9 H, s); 3.21 (2 H, dd, J=6.8+12.7 Hz); 3.26-3.34 (2 H, m); 4.05 (2 H, t, J=6.8 Hz); 7.90 (1 H, t, J=5.9 Hz); 10.00 (1 H, s).

$^{13}$C-NMR (DMSO-d$_6$): 13.91; 22.03; 23.16; 25.13; 28.16; 28.56-28.97 (10 C); 31.22; 36.30; 52.14; 63.24; 64.94; 152.69; 154.11.

Signals are superimposed in the aliphatic region.

Example 4

Stage 1

4-(Dimethylamino-1-ethyl)allophanic acid ethyl ester (US-646)

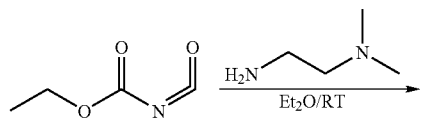

21

-continued

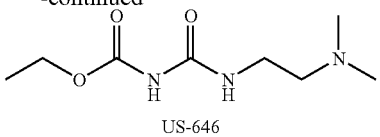
US-646

A solution of ethyl isocyanatoformate (500 mg, 4.2 mmol) in absolute diethyl ether (15 mL) was added dropwise to a solution of $N^1.N^1$-dimethylethane-1,2-diamine (440 mg, 550 µL, 5 mmol) in diethyl ether (25 mL) and stirred for 2 h at room temperature. The precipitate was filtered off and the filtrate was concentrated under vacuum.

Yield: 772 mg (90%), white solid

Melting point: 40-67° C.

$^1$H-NMR (DMSO-d$_6$): 1.19 (3 H, t, J=6.8 Hz); 2.13 (6 H, s); 2.31 (2 H, t, J=6.3 Hz); 3.21 (2 H, q J=5.8 Hz); 4.09 (2 H, q J=6.8 Hz); 7.91 (1 H, t, J=4.8 Hz); 9.70-10.10 (1 H, br s).

Stage 2

(4-Trimethylamino-1-ethyl)allophanic acid ethyl ester iodide (US-647)

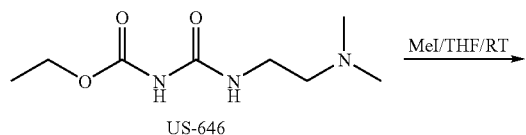

US-646 →(MeI/THF/RT)

22

-continued

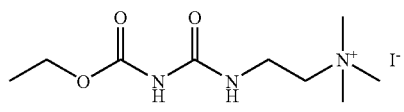
US-647

Methyl iodide (1.18 g, 500 µL, 8.4 mmol) was added to a solution of US-646 (340 mg, 1.67 mmol) in absolute tetrahydrofuran (20 mL) and stirred for 4 h at room temperature. The precipitate was filtered off and washed with tetrahydrofuran.

Yield: 530 mg (92%), white solid

Melting point: 172-175° C.

$^1$H-NMR (DMSO-d$_6$): 1.20 (3 H, t, J=7.2 Hz); 3.10 (9 H, s); 3.42 (2 H, t, J=5.8 Hz); 3.61 (2 H, m); 4.11 (2 H, q J=6.8 Hz); 8.12 (1 H, t, J=5.8 Hz); 10.19 (1 H, s).

$^{13}$C-NMR (DMSO-d$_6$): 14.2; 33.7; 52.5 (3 C); 61.9; 64.1; 153.1; 154.3.

Example 5

Synthesis of 4-(N,N,N-trimethylaminoethyl)allophanic acid (3-hexadecyloxy-2-methoxypropan-1-yl ester iodide

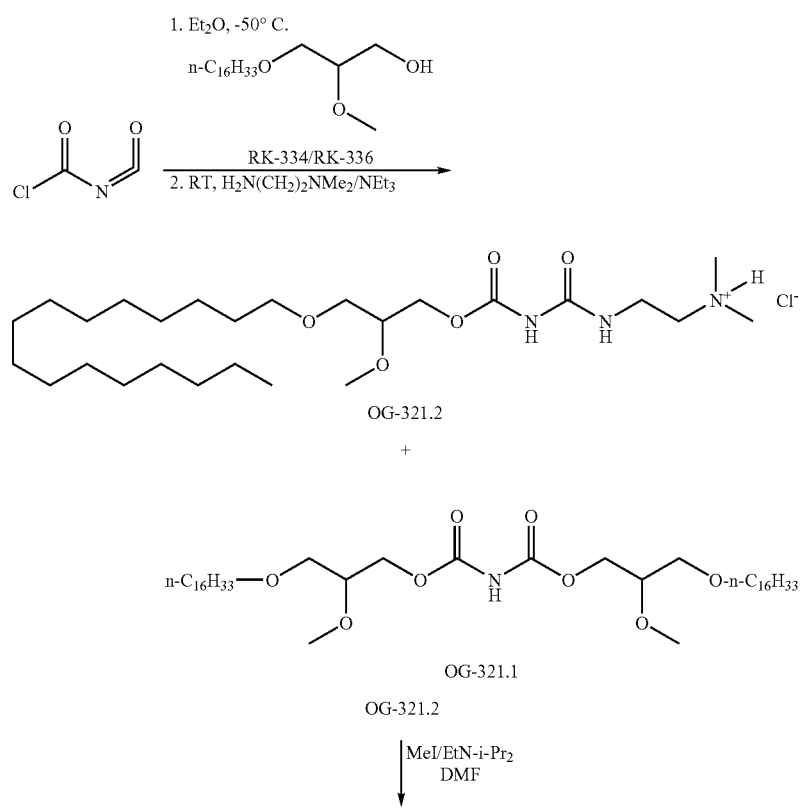

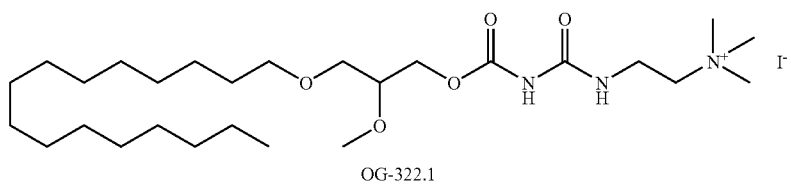

OG-322.1

Stage 1 cis-5-Methoxy-2-phenyl-[1,3]dioxan (RK-330)

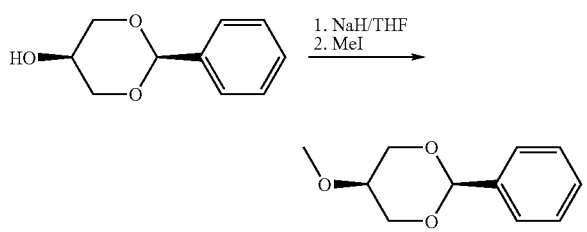

A solution of cis-1,3-benzylidene glycerol (5.47 g, 30 mmol) in anhydrous tetrahydrofuran (50 mL) was added dropwise to a mixture of 55% oily sodium hydride suspension (1.96 g, 45 mmol) in anhydrous tetrahydrofuran. When evolution of hydrogen had ceased, a solution of methyl iodide (8.52 g, 3.74 mL, 60 mmol) in anhydrous tetrahydrofuran (20 mL) was added, while cooling with ice, and then stirred overnight at room temperature. The reaction mixture was filtered, the filtrate was evaporated to dryness under vacuum and the residue was taken up in toluene. The toluene solution was filtered, the filtration residue was washed with toluene (25 mL) and the filtrate was concentrated under vacuum. After crystallization of the residue (yellow solid) the white oil was decanted off.

Yield: 5.57 g (95%)

$^1$H-NMR (CDCl$_3$): 3.18 (1 H, q, J=2 Hz); 3.48 (3 H, s); 4.05 (2 H, dd, J=2 and 12.5 Hz); 4.37 (2 H, d, J=12.5 Hz); 5.56 (1 H, s); 7.31-7.37 (4 H, m); 7.50-7.53 (1 H, m).

Stage 2

2-Methoxypropane-1,3-diol (RK-331)

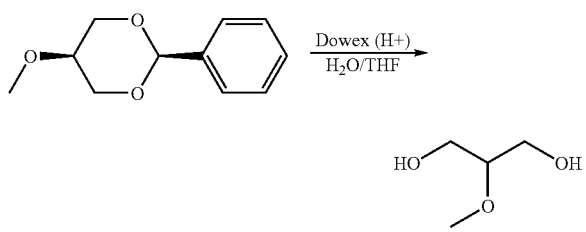

Strongly acidic Dowex ion exchanger (2 g) was added to a solution of RK-330 (5.55 g, 28 mmol) in a mixture of water (10 mL)/tetrahydrofuran (20 mL) and was heated under reflux for 5 h. The reaction mixture was then filtered and the filtration residue was washed with distilled water (25 mL). The filtrate was concentrated under vacuum and the residue was taken up in water (100 mL). The aqueous phase was extracted with tert-butyl methyl ether (3×25 mL). The aqueous phase was concentrated under vacuum and the residue was dissolved in pyridine (3×10 mL) for azeotropic drying and was concentrated each time.

Yield: 2.60 g (88%), colourless liquid $^1$H-NMR (DMSO-d$_6$): 3.12 (1 H, dt, J=4.2, 10.4 Hz); 3.32 (3 H, s); 3.34-3.47 (4 H, m); 4.45 (2 H, t, J=6 Hz).

Stage 3

3-Hexadecyloxy-2-methoxy-propan-1-ol (RK-334)

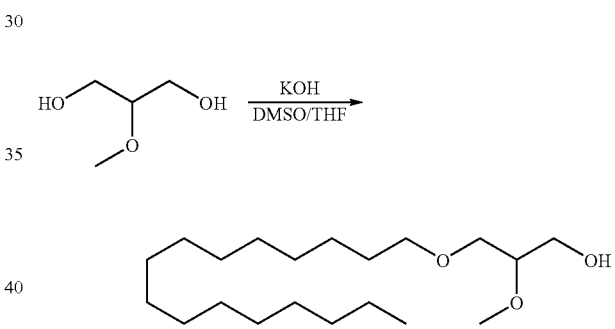

Powdered potassium hydroxide (1.4 g, 25 mmol) was added to a solution of RK-331 (2.60 g, 24.5 mmol) in anhydrous dimethylsulphoxide (20 mL) and anhydrous tetrahydrofuran (20 mL) and then a solution of iodohexadecane (4.58 g, 13 mmol) in anhydrous tetrahydrofuran (20 mL) was added dropwise and the mixture was stirred for 16 h at room temperature. The suspension was concentrated under vacuum, water (40 mL) was added to the residue and it was extracted with tert-butyl methyl ether (3×50 mL). The combined organic phases were dried over sodium sulphate, filtered and concentrated to dryness. The residue was purified by flash chromatography (100 g, 20×4 cm) with tert-butyl methyl ether/cyclohexane (2:1).

Yield: 2.00 g (46% based on iodohexadecane), colourless solid

Melting point: 31-33° C.

$^1$H-NMR (CDCl$_3$): 0.88 (3 H, t, J=7.2 Hz); 1.22-1.35 (26 H, m); 1.57 (2 H, 7.1 Hz); 2.14 (1 H, dd, J=5.4 and 7.0 Hz); 3.40-3.48 (1 H, m); 3.47 (3 H, s); 3.48-3.58 (2 H, m); 3.61-3.68 (1 H, m); 3.73-3.79 (1 H, m).

Stage 4

4-(N,N-Dimethylaminoethyl)allophanic acid 3-hexadecyloxy-2-methoxypropan-1-yl ester hydrochloride (OG-321.2) and imidodicarboxylic acid di-3-hexadecyloxy-2-methoxypropan-1-yl ester (OG-321.1)

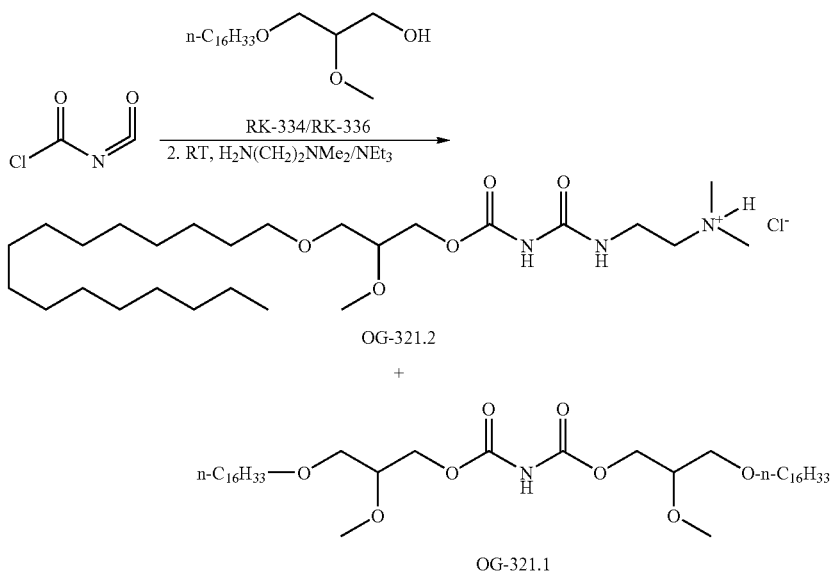

A solution of RK-334 (3.14 g, 9.5 mmol) in absolute diethyl ether (40 mL) was slowly added dropwise to a solution of chlorocarbonyl isocyanate (0.76 mL, 9.5 mmol) in absolute diethyl ether (50 mL) at −50° C. under argon. The reaction solution was stirred for 1 h under argon at −60° C. and then its temperature was raised to 0° C. within one hour. Then a solution of N,N-dimethylethylenediamine (1.05 mL, 840 mg, 9.5 mmol) and triethylamine (1.0 mL) in absolute diethyl ether (50 mL) was slowly added dropwise to the reaction mixture at 0° C. The reaction mixture was stirred at room temperature for 16 h, acidified with hydrogen chloride in diethyl ether and stirred for 1 h at room temperature. The resultant solid was filtered off, washed with diethyl ether and dried under vacuum. The white solid was suspended in water (100 mL). The suspension was distributed into two centrifuge tubes, centrifuged 2×20 min at 5000 rev/min and then decanted. The amorphous solid isolated (OG-321.2) was dried over phosphorus pentoxide, under vacuum.

OG-321.2

Yield: 310 mg (7%), white solid

Melting point: 59-63° C.

$^1$H-NMR (DMSO-$d_6$): 0.85 (3 H, t, J=6.8 Hz); 1.18-1.24 (26 H, m); 1.45-1.50 (2 H, m); 2.79 (6 H, s); 3.00-3.56 (9 H, m); 3.32 (3 H, s); 4.04 (1 H, dd, J=5.6 and 11.6 Hz); 4.21 (1 H, dd, J=3.6 and 11.2 Hz); 7.98 (1 H, br. t, J=5.9 Hz); 9.70 (1 H, br s); 10.17 (1H, s).

$^{13}$C-NMR (DMSO-$d_6$): 13.94; 22.05; 25.55; 28.64; 28.77; 28.96; 29.06; 31.23; 34.53; 38.88; 42.45 (2 C); 56.08; 57.04; 64.15; 68.74; 70.53; 77.21; 152.93; 153.75.

Signals are superimposed in the aliphatic region.

The combined diethyl ether filtrates were concentrated and dried under vacuum, isolating OG-321.1.

OG-321.1

Yield: 920 mg (52%), white solid

Melting point: 40-42° C.

$^1$H-NMR (DMSO-$d_6$+CDCl$_3$): 0.81 (6 H, t, J=6.8 Hz); 1.10-1.30 (55 H, m); 1.40-1.54 (4 H, m); 2.80-3.55 (6 H, m); 3.34 (6 H, s); 4.01 (1 H, d, J=6.8 Hz); 4.04 (1 H, d, J=5.8 Hz); 4.18 (1 H, dd, J=2.0 and 3.9 Hz); 4.21 (1 H, dd, J=2.0 and 3.9 Hz); 10.20 (1 H, s).

Stage 5

4-(N,N,N-Trimethylaminoethyl)allophanic acid 3-hexadecyloxy-2-methoxypropan-1-yl ester iodide (OG-322.1)

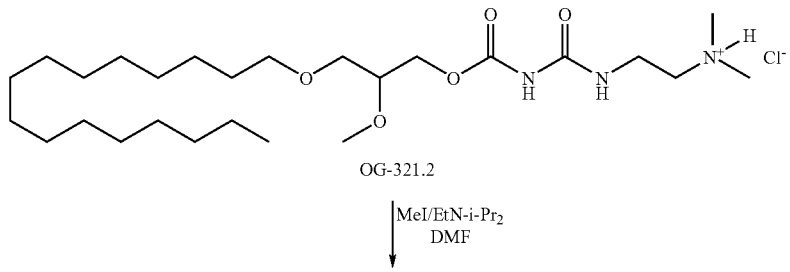

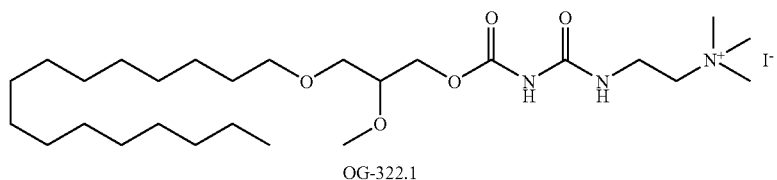

OG-322.1

Methyl iodide (125 μL, 280 mg, 2 mmol) was added to a mixture of OG-321.1 (210 mg, 0.40 mmol) in absolute N,N-dimethylformamide (10 mL) and ethyl diisopropylamine (136 μL, 103 mg, 0.80 mmol) and was then stirred for 2.5 h at 50° C. The reaction mixture was evaporated to dryness under vacuum, the residue was taken up in dichloromethane, concentrated again and then dried under vacuum. Water (25 mL) was added to the residue (400 mg) and it was stirred for 30 min at room temperature. The suspension was centrifuged (20 min at 5000 rev/min) and then decanted. The amorphous solid isolated was taken up in methanol, the resultant mixture was concentrated and the residue was dried over phosphorus pentoxide, under vacuum.

Yield: 120 mg (48%), white solid
Melting point: 136-141° C.

$^1$H-NMR (DMSO-$d_6$): 0.80-0.90 (3 H, m); 1.20-1.35 (26 H, m); 1.40-1.50 (2 H, m); 3.10 (9 H, s); 3.32 (3 H, s); 3.20-3.64 (9 H, m); 4.05 (1 H, dd, J=5.2 and 11.2 Hz); 4.22 (1 H, dd, J=5.2 and 11.2 Hz); 8.06 (1 H, brt, J=5.9 Hz); 10.22 (1 H, s).

$^{13}$C-NMR (DMSO-$d_6$); 13.93; 22.04; 25.54; 28.64; 28.77; 28.96; 29.05; 31.22; 33.76; 52.47 (3 C); 57.04; 63.99; 64.19; 68.73; 70.52; 77.19; 152.67; 153.84.

Signals are superimposed in the aliphatic region.

Example 6

Synthesis of 4-(N,N,N-trimethylaminoethyl)allophanic acid (cis-5-hexadecyloxymethyltetrahydrofuran-2-yl)methyl ester iodide

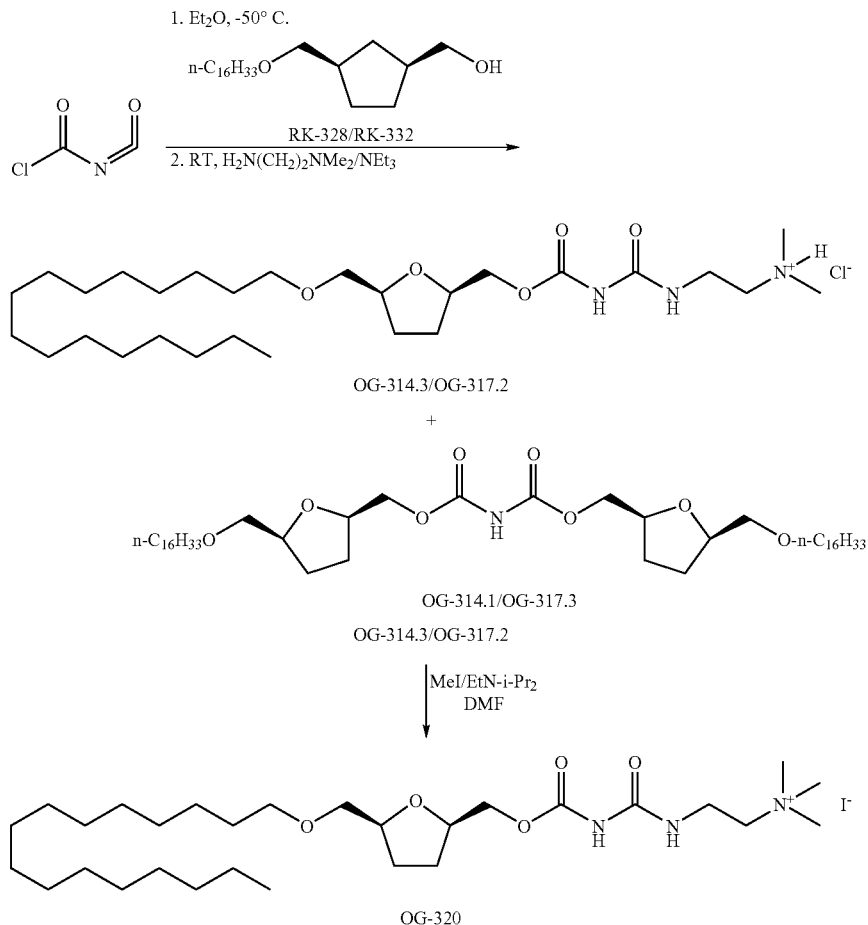

Stage 1

Synthesis of (5-hydroxymethylfuran-2-yl)methanol (RK-325)

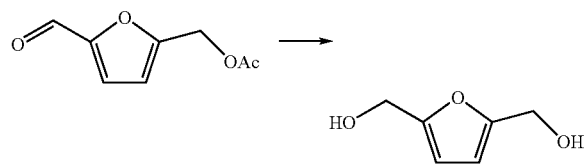

Sodium borane (1.2 g, 32 mmol) was added to a solution of 5-formylfuran-2-yl-methyl formate (5.05 g, 30 mmol) in absolute ethanol (150 mL) at 0° C. Then it was warmed to room temperature and stirred for 48 hours. Then it was cooled to 0° C. and acidified with concentrated hydrochloric acid to pH 4 and then neutralized immediately with 5% sodium hydrogen carbonate solution. The mixture was filtered and the filtrate was evaporated to dryness under vacuum. The residue was taken up in ethanol (30 mL), filtered, and the filtrate was concentrated to dryness.

Yield 3.48 g (91%); slightly brown oil $^1$H-NMR (CDCl$_3$): 4.58 (4 H, s); 6.23 (2 H, s);

Stage 2

Synthesis of (5-hydroxymethyltetrahydrofuran-2-yl)methanol (RK-325)

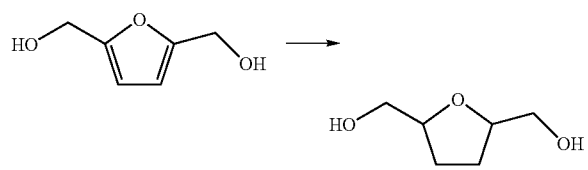

Raney nickel [ethanol was added three times to 50% commercial aqueous Raney nickel suspension (5 mL) from Acros, and decanted] was added to a solution of (5-hydroxymethyl-furan-2-yl)methanol (RK-325) (3.46 g, 27 mmol) in absolute ethanol (100 mL), and hydrogenated overnight at room temperature and at a pressure of 2 bar (hydrogen consumption 61 mmol). The reaction mixture was filtered and the filtrate was concentrated under vacuum.

Yield 3.17 g (89%); colourless liquid $^1$H-NMR (CDCl$_3$): 1.78-2.00 (4H, m); 3.54 (2H, dd, J=5.2 and 11.2 Hz); 3.79 (2H, dd, J=1.6 and 11.2 Hz), 4.07-4.14 (2H, m).

Stage 3

Synthesis of (5-hexadecyloxymethyltetrahydrofuran-2-yl)methanol (RK-328)

Pulverized potassium hydroxide (1.345 g, 24 mmol) was added to a solution of RK-325 (3.16 g, 23.9 mmol) in anhydrous dimethylsulphoxide (20 mL) and anhydrous tetrahydrofuran (20 mL). A solution of 1-iodohexadecane (3.52 g, 10 mmol) in anhydrous tetrahydrofuran (20 mL) was added dropwise to this suspension at room temperature. Then it was stirred for 16 hours at room temperature. The suspension was concentrated under vacuum, and water (40 mL) was added to the residue. Then it was extracted with tert-butyl methyl ether (3×50 mL). The combined organic extracts were dried over sodium sulphate, filtered and evaporated to dryness under vacuum. The residue was purified by flash chromatography (100 g, 23×4 cm) with tert-butyl methyl ether/cyclohexane (2:1).

Yield 1.76 g (49% based on n-C16H33I); white solid

Melting point 29-30° C.

$^1$H-NMR (CDCl$_3$): 0.88 (3H, t, J=6.8 Hz); 1.25-1.38 (24 H, m); 1.59 (2H, dt, J=2.8 and 7.0 Hz); 1.89-1.96 (4H, m); 2.69 (1H, dd, J=4.3 and 8.4 Hz); 3.40-3.51 (6H, m); 3.60 (1H, dd, J=3.0 and 10.2 Hz); 3.80 (1H, ddd, J=3.9, 4.1 and 12.4 Hz); 4.10 (2H, m).

Stage 4

2-(N,N-Dimethylaminoethyl)allophanic acid-(cis-5-hexadecyloxymethyltetrahydrofuran-2-yl)methyl ester hydrochloride (OG-317.2) and imidodicarboxylic acid-di(cis-5-hexadecyloxymethyltetrahydrofuran-2-yl)methyl ester (OG-317.3)

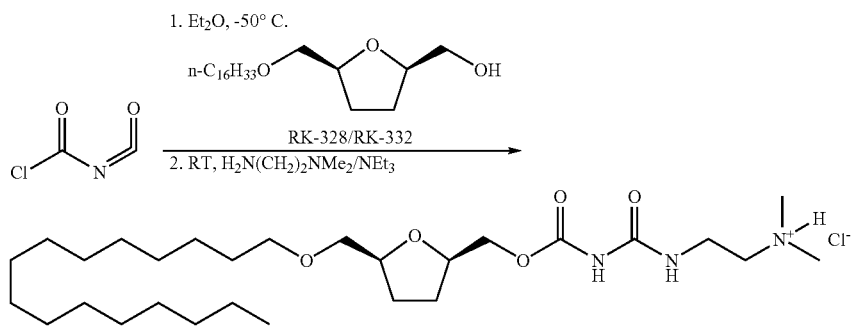

OG-314.3/OG-317.2

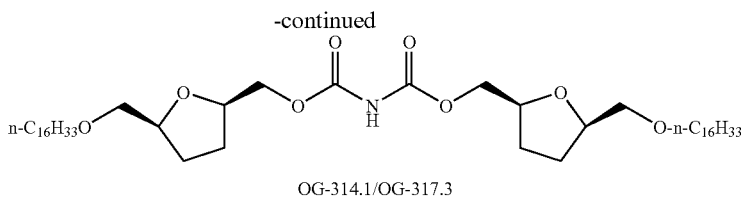

OG-314.1/OG-317.3

A solution of RK-332 (1.8 g, 5 mmol) in absolute diethyl ether (40 mL) was slowly added dropwise to a solution of chlorocarbonyl isocyanate (0.40 mL, 5 mmol) in absolute diethyl ether (30 mL) at −50° C. under argon. The reaction solution was stirred for 1 h at −60° C. under argon and was then warmed to 0° C. within one hour. A solution of N,N-dimethylethylenediamine (0.55 mL, 440 mg, 5 mmol) and tri-ethylamine (0.5 mL) in absolute diethyl ether (30 mL) was then slowly added dropwise to the reaction mixture at 0° C. The reaction mixture was stirred at room temperature for 16 h, then it was acidified with hydrogen chloride in diethyl ether and stirred for 1 h at room temperature. The resultant solid was filtered with suction, washed with diethyl ether and dried under vacuum. The white solid (2.88 g) was suspended in water (100 mL). The suspension was distributed into two centrifuge tubes, centrifuged 2×20 min at 5000 rev/min and then decanted. The amorphous solid isolated (OG-317.2) was dried over phosphorus pentoxide, under vacuum.

OG-317.2

Yield 500 mg (18%), white solid

Melting point: 84-85° C.

$^1$H-NMR (DMSO-d$_6$): 0.86 (3 H, t, J=6.6 Hz); 1.14-1.34 (26 H, m); 1.42-1.52 (2 H, m); 1.56-1.70 (2 H, m); 1.82-1.89 (2 H, m); 2.76 (6 H, s); 3.15 (2 H, dd, J=5.5 and 5.5 Hz); 3.30-3.40 (4 H, m); 3.50 (2 H, dd, J=6.2 and 11.7 Hz); 3.97 (2 H, dd, J=6.4 and 10.8 Hz); 4.00-4.08 (1 H, m); 4.11 (1 H, dd, J=3.6 and 11.2 Hz); 7.99 (1 H, t, J=5.5 Hz); 10.18 (1 H, s).

$^{13}$C-NMR (DMSO-d$_6$): 13.94; 22.06; 25.61; 27.00; 27.50; 28.65-29.16 (11 C); 31.24; 34.60; 42.52; 56.12; 67.16; 70.42; 72.84; 76.21; 78.10; 152.97; 153.82.

Signals are superimposed in the aliphatic region.

The combined diethyl ether filtrates were concentrated and dried under vacuum, and OG-317.3 was isolated.

OG-317.3

Yield 610 mg (31%), white solid

Melting point: 42-45° C.

$^1$H-NMR (DMSO-d$_6$+CDCl$_3$): 0.80-0.88 (6 H, m); 1.14-1.34 (52 H, m); 1.42-1.52 (4 H, m); 1.58-1.72 (4 H, m); 1.80-2.00 (4 H, m); 3.26-3.40 (8 H, m); 3.90-4.16 (8 H, m); 10.48 (1 H, s).

4-(N,N,N-trimethylaminoethyl)allophanic acid (cis-5-hexadecyloxymethyl tetrahydrofuran-2-yl)methyl ester iodide (OG-320)

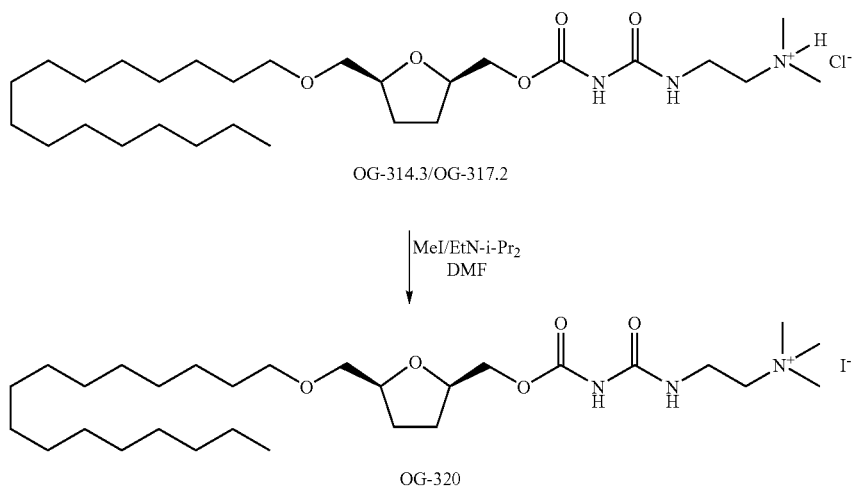

Methyl iodide (340 µL, 775 mg, 5.5 mmol) was added to a mixture of OG-314.3/OG-317.2 (600 mg, 1.1 mmol) in absolute N,N-dimethylformamide (25 mL) and ethyl diisopropylamine (370 µL, 2.2 mmol) and was then stirred for 2.5 h at 50° C. The reaction mixture was concentrated to dryness under vacuum, the residue was taken up in dichloromethane, the resultant suspension was concentrated again and the solid was dried under vacuum. Water was added to the residue (1.33 g) and it was stirred at room temperature for 30 min. The suspension was centrifuged (20 min at 5000 rev/min) and then decanted. Methanol was added to the amorphous solid that had been isolated, the suspension was concentrated and the residue was then dried over phosphorus pentoxide, under vacuum.

Yield: 620 mg (86%), white solid

Melting point: 96-101° C.

$^1$H-NMR (DMSO-d$_6$): 0.85 (3 H, t, J=6.4 Hz); 1.12-1.36 (26 H, m); 1.40-1.50 (2 H, m); 1.50-1.68 (2 H, m); 1.80-2.00 (2 H, m); 3.10 (9 H, s); 3.15-3.50 (4 H, m); 3.54-3.64 (2 H, m); 3.97 (2 H, dd, J=5.9+10.8 Hz); 4.00-4.08 (1 H, m); 4.12 (1 H, dd, J=2.9 and 10.8 Hz); 8.07 (1 H, t, J=5.8 Hz); 10.21 (1 H, s).

$^{13}$C-NMR (DMSO-d$_6$): 13.93; 22.06; 25.61; 27.00; 27.50; 28.65-29.16 (11 C); 31.24; 33.77; 52.46; 52.49; 52.53; 64.02; 67.20; 70.42; 72.84; 76.21; 78.09; 152.73; 153.89.

Signals are superimposed in the aliphatic region.

Example 7

Synthesis of 4-(N,N,N-trimethylaminoethyl)allophanic acid (2-hexadecyloxymethyltetrahydrofuran-2-yl)methyl ester iodide

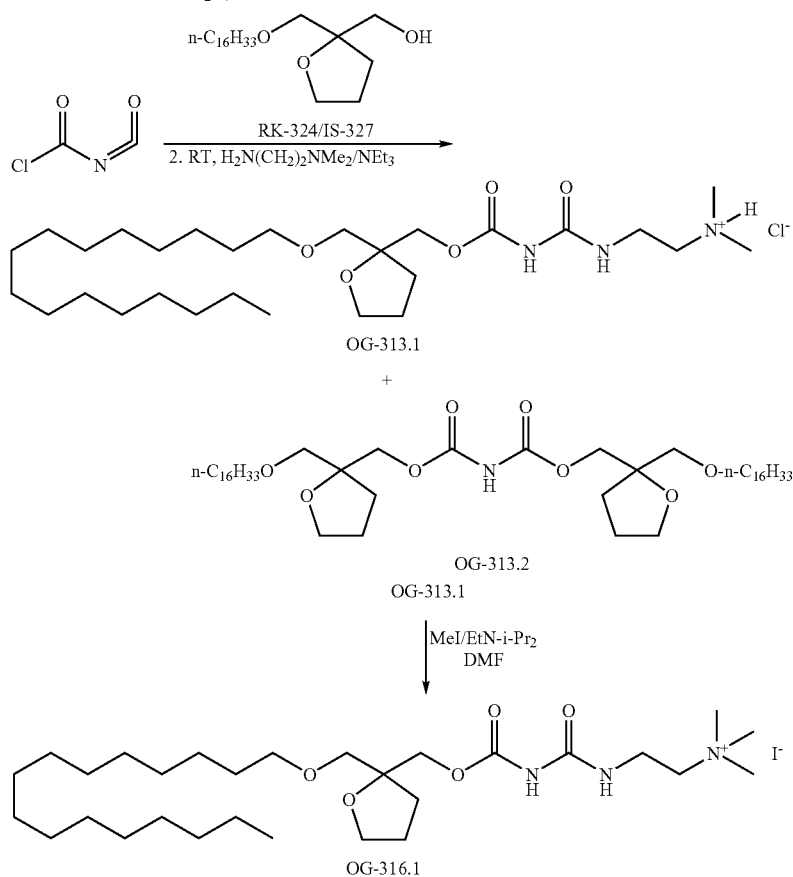

Stage 1

Tetrahydrofuran-2-carboxylic acid methyl ester (RK-321)

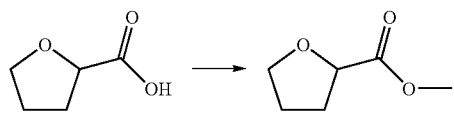

A solution of tetrahydrofuran-2-carboxylic acid (37.7 g, 325 mmol) in methanol containing hydrogen chloride (200 mL) was stirred overnight at room temperature. The solvent was removed under vacuum and the residue was taken up in dichloromethane (150 mL). The solution was washed with sodium hydrogen carbonate solution and water (in each case 2×100 mL), dried over sodium sulphate, filtered and concentrated to dryness.

Yield: 32.7 g (78%)

$^1$H-NMR (CDCl$_3$): 1.84-2.35 (4H, m); 3.74 (3H, s); 3.92 (1H, dt, J=5.6 and 7.2 Hz); 4.01 (1H, dt, J=6.0 and 8.4 Hz); 4.45 (1H, dd, J=5.6 and 8.4 Hz).

Stage 2

(2-Hydroxymethyltetrahydrofuran-2-yl)methanol (RK-322)

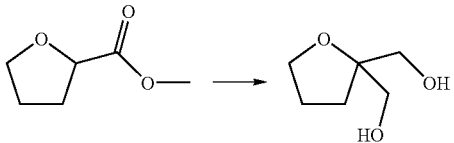

A 1.2 M solution of diisobutylaluminium hydride in toluene (45 mmol, 37.5 mL) was added to a solution of RK-321 (5.25 g, 40 mmol) in anhydrous tetrahydrofuran (50 mL) at −78° C., so that the internal temperature did not exceed −65° C. It was then stirred for 90 min at −78° C. and then anhydrous methanol (6 mL) was added, so that the internal temperature remained below −50° C. Then the reaction mixture was warmed slowly to 5° C. This solution was added dropwise to a cooled solution of sodium hydroxide (13.0 g, 0.325 mmol), water (45 mL) and 37% formalin (56.5 mL, 0.975 mmol), with the internal temperature remaining below 12° C. After 5 min, formic acid (1.7 mL) was added to the reaction mixture and it was heated to 65° C. Then the solvents were distilled off under vacuum. Dichloromethane (25 mL) was added to the solid residue and it was treated for 15 min in an ultrasonic bath. The suspension was filtered and the residue was washed with dichloromethane (100 mL). The combined filtrates were concentrated under vacuum and the residue was distilled in a bulb tube (bath temperature 140° C., 0.14 mbar).

Yield: 1.64 g (31%); white solid, melting at approx. 40° C.

$^1$H-NMR (CDCl$_3$): 1.78 (2H, dt, J=0.8 and 7.6 Hz); 1.92-2.00 (5H, m); 3.55 (2H, br d, J=10.8 Hz); 3.63 (2H, br d, J=10.8 Hz); 3.89 (2H, t, J=6.4 Hz).

vacuum. The residue was purified by flash chromatography (90 g, 20×4 cm) with tert-butyl methyl ether/cyclohexane (3:1).

Yield 744 mg (51% based on n-C16H33I); colourless oil $^1$H-NMR (CDCl$_3$): 0.89 (3H, t, J=7.2 Hz); 1.26 (26 H, br s); 1.52-1.59 (2H, m); 1.76-1.96 (4H, m); 2.21 (2H, t, J=7.2); 3.34-3.62 (6H, m); 3.86 (2H, dt, J=1.2 and 6.6 Hz).

$^{13}$C-NMR (CDCl$_3$): 14.25; 22.82; 26.23; 29.48; 29.58; 29.71; 29.80; 30.65; 32.03; 66.60; 68.61; 72.07; 74.41; 83.96;

Stage 4

4-(N,N-Dimethylaminoethyl)allophanic acid-(2-hexadecyloxymethyl tetrahydrofuran-2-yl)methyl ester (OG-313.1) and imidodicarboxylic acid-di-(2-hexadecyloxymethyltetrahydrofuran-2-yl)methyl ester (OG-313.2)

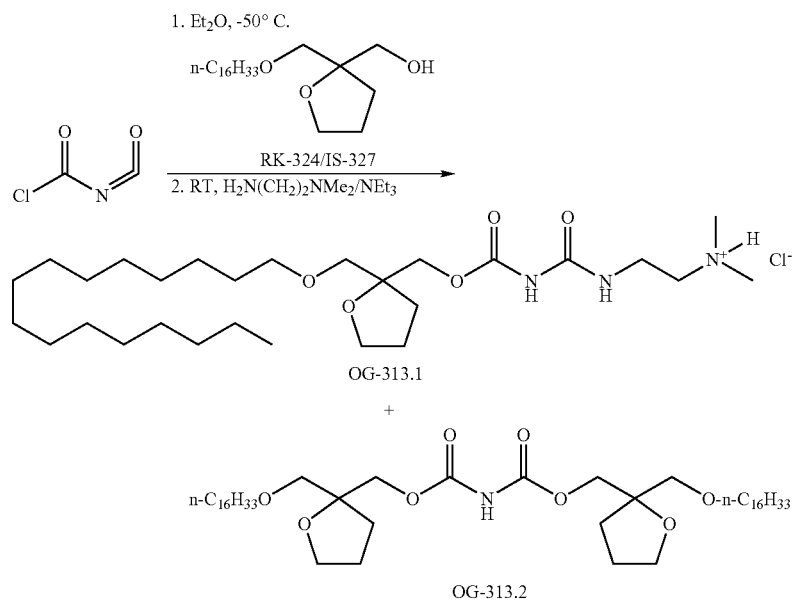

Stage 3

(2-Hexadecyloxymethyl-tetrahydrofuran-2-yl)-methanol

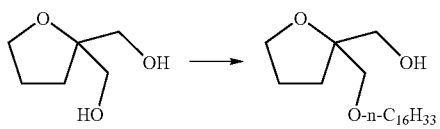

Pulverized potassium hydroxide (684 mg, 12.2 mmol) was added to a solution of RK-322 (1.60 g, 12.2 mmol) in anhydrous dimethylsulphoxide (10 mL) and anhydrous tetrahydrofuran (10 mL). A solution of 1-iodohexadecane (1.41 g, 4 mmol) in anhydrous tetrahydrofuran (6 mL) was added dropwise to this suspension at room temperature. Then it was stirred for 16 hours at room temperature. The suspension was concentrated under vacuum and water (20 mL) was added to the residue. Then it was extracted with tert-butyl methyl ether (3×25 mL). The combined organic extracts were dried over sodium sulphate, filtered and evaporated to dryness under A solution of IS-320 (1.8 g, 5 mmol) in absolute diethyl ether (26 mL) was slowly added dropwise to a solution of chlorocarbonyl isocyanate (0.40 mL, 5 mmol) in absolute diethyl ether (30 mL) at −50° C. under argon. The reaction solution was stirred for 1 h at −60° C. under argon and was then warmed to 0° C. within one hour. A solution of N,N-dimethylethylenediamine (0.55 mL, 440 mg, 5 mmol) and triethylamine (0.5 mL) in absolute diethyl ether (30 mL) was then slowly added dropwise to the reaction mixture at 0° C. The reaction mixture was stirred for 16 h at room temperature, then it was acidified with hydrogen chloride in diethyl ether and stirred for 1 h at room temperature. The resultant solid was filtered with suction, washed with diethyl ether and dried under vacuum. The white solid was suspended in water (100 mL). The suspension was distributed into two centrifuge tubes, centrifuged 2×20 min at 5000 rev/min and then decanted. The isolated solid (OG-313.1) was dried over phosphorus pentoxide, under vacuum.

Yield: 206 mg (7%), white greasy solid

OG-313.1

$^1$H-NMR (DMSO-d$_6$): 0.80-0.85 (3 H, m); 1.24-1.40 (26 H, m); 1.40-1.46 (2 H, m); 1.72-1.96 (4 H, m); 2.79 (6 H, s);

3.00-3.45 (6 H, m); 3.50-3.62 (2 H, m); 3.70-3.80 (2 H, m); 4.00 (1 H, d, J=10.8 Hz); 4.05 (1 H, d, J=11.7 Hz); 7.90-8.10 (1 H, m); 10.13 (1 H, s); 10.40 (1 H, br s).

$^{13}$C-NMR (DMSO-d$_6$): 13.92; 22.06; 25.40; 25.56; 28.65; 28.75; 28.76; 28.98; 30.06; 31.24; 34.43; 42.26 (2 C); 55.75; 66.60; 67.70; 70.72; 72.31; 82.37; 152.88; 153.73.

Signals are superimposed in the aliphatic region.

4-(N,N,N-trimethylaminoethyl)allophanic acid (2-hexadecyloxymethyl tetrahydrofuran-2-yl)methyl ester iodide (OG-316.1)

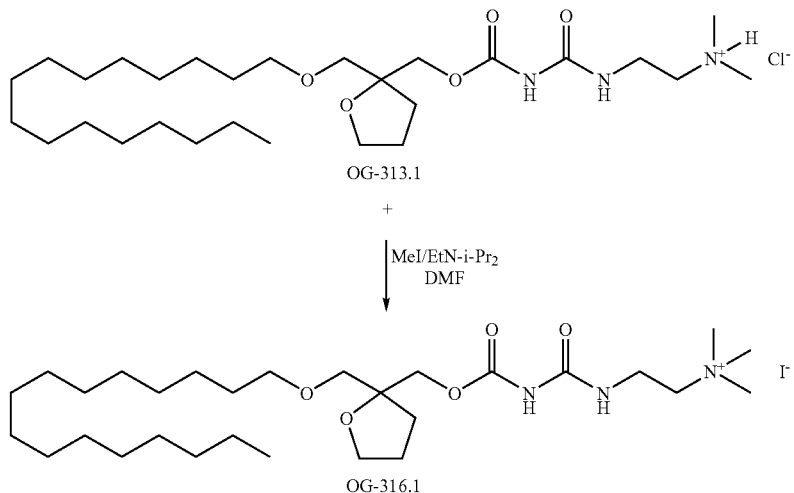

Methyl iodide (96 μL, 220 mg, 1.55 mmol) was added to a mixture of OG-313.1 (170 mg, 0.31 mmol) in absolute N,N-dimethylformamide (10 mL) and ethyl diisopropylamine (105 μL, 80 mg, 0.62 mmol) and it was then stirred for 2.5 h at 50° C. The reaction mixture was evaporated to dryness under vacuum, the residue was taken up in dichloromethane, the resultant suspension was concentrated again and the solid was dried under vacuum. Water (30 mL) was added to the residue and it was stirred at room temperature for 30 min. The suspension was centrifuged (20 min at 5000 rev/min) and then decanted. Methanol was added to the amorphous solid that had been isolated, the suspension was concentrated and the residue was then dried over phosphorus pentoxide, under vacuum.

Yield: 120 mg (58%), white solid

Melting point: 79-85° C.

$^1$H-NMR (DMSO-d$_6$): 0.86 (3 H, t, J=6.7 Hz); 1.15-1.36 (26 H, m); 1.45-1.53 (2 H, m); 1.66-1.95 (4 H, m); 3.10 (9 H, s); 3.20-3.48 (6 H, m); 3.54-3.64 (2 H, m); 3.66-3.80 (2 H, m); 3.99 (1 H, d, J=10.8 Hz); 4.05 (1 H, d, J=11.7 Hz); 8.07 (1 H, br t, J=6.3 Hz); 10.21 (1 H, s).

$^{13}$C-NMR (DMSO-d$_6$): 13.93; 22.04; 25.38; 25.54; 28.63; 28.72; 28.97; 30.08; 31.24; 33.74; 52.47; 63.99; 66.65; 67.69; 70.70; 72.25; 82.37; 152.76; 153.91.

Signals are superimposed in the aliphatic region.

Example 8

Stage 1

4-(Dimethylamino-1-ethyl)allophanic acid phenyl ester (US-605)

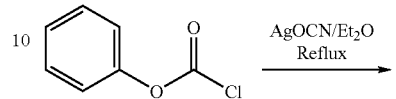

-continued

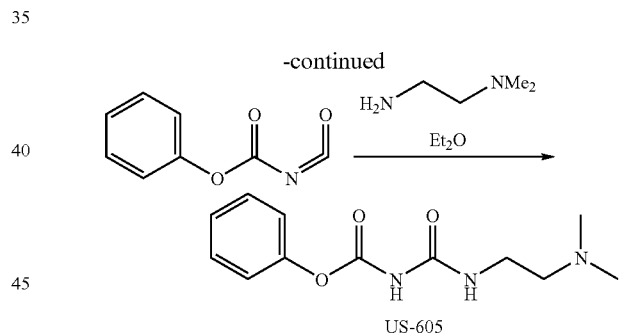

A solution of phenyl chloroformate (780 mg, 630 μL, 5 mmol) in absolute diethyl ether (20 mL) was added dropwise to a suspension of silver cyanate (890 mg, 6 mmol) in absolute diethyl ether (20 mL) and it was then stirred for 1 h under reflux. After cooling, the precipitated solid was filtered off. The filtrate was added dropwise to a solution of N$^1$.N$^1$-dimethylethane-1,2-diamine (530 mg, 660 μL, 6 mmol) in diethyl ether (25 mL), and a white solid (427 mg) was precipitated, and was filtered off. The filtrate was concentrated under vacuum (660 mg). The residue was purified by flash chromatography (18 g, 20×2.0 cm) with ethyl acetate/cyclohexane (1:1) and 1% triethylamine.

Yield: 230 mg (18%), yellow oil $^1$H-NMR (DMSO-d$_6$): 2.16 (6 H, s); 2.34 (2 H, t, J=6.8 Hz); 3.14 (2 H, dd, J=12.0 and 6.0 Hz); 6.75 (1 H, m); 7.06 (2 H, d, J=7.8 Hz); 7.10-7.21 (1 H, m); 7.36 (2 H, t, J=7.8 Hz); 7.60 (1 H, br t, J=5.3 Hz).

$^{13}$C-NMR (DMSO-d$_6$): 36.6; 45.2 (2 C); 58.2; 121.6 (2 C); 124.7; 129.3 (2 C); 151.1; 154.2; 157.3.

Stage 2

4-(Trimethylamino-1-ethyl)allophanic acid phenyl ester iodide (US-608)

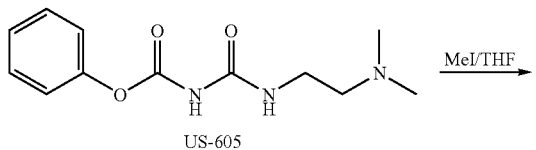

Methyl iodide (355 mg, 150 μL, 2.5 mmol) was added to a solution of US-605 (130 mg, 0.52 mmol) in absolute tetrahydrofuran (20 mL) and it was stirred at room temperature for 4 h. The precipitate was filtered off and dried under vacuum.

Yield: 100 mg (49%), white, hygroscopic foam

Melting point: 30-125° C.

$^1$H-NMR (DMSO-$d_6$, after 5 days): 3.11 (9 H, s); 3.34 (2 H, t, J=6.3 Hz); 3.44 (2 H, m); 6.67 (1 H, t, J=5.5 Hz); 6.74 (1 H, s); 6.75 (2 H, m); 7.15 (2 H, dd, J=8.6 and 8.6 Hz); 9.33 (1 H, br s).

$^{13}$C-NMR (DMSO-$d_6$): 33.8; 52.6 (3 C); 64.6 (2 C); 115.1 (2 C); 118.7; 129.3 (3 C); 1.54.4; 157.2; 157.7.

The substance is a tautomeric mixture and also contains tetrahydrofuran.

Example 9

Stage 1

Biphenyl-4-yl chloroformate (US-617)

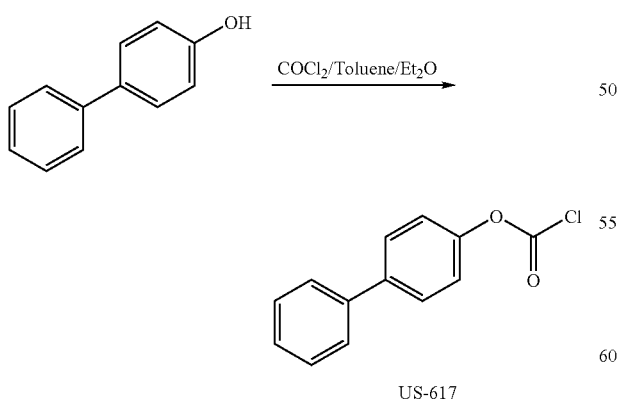

4-Hydroxybiphenyl (2.62 g, 15.4 mmol) in absolute toluene/diethyl ether (60/30 mL) was added dropwise in the space of 30 minutes, with ice cooling, to a solution of phosgene (1.98 g, 20 mmol) in absolute toluene (20 mL). Then, at −3° C., N,N-dimethylaniline (1.86 g, 1.95 mL, 15.4 mmol) in absolute toluene (10 mL) was added dropwise and it was stirred overnight, while slowly warming to room temperature. After cooling to 0° C. again, water (30 mL) was slowly added dropwise, then the organic phase was washed with 0.1N HCl, 0.1N NaOH and water (each 2×100 mL), dried over sodium sulphate and concentrated under vacuum.

Yield: 2.69 g (75%), colourless oil $^1$H-NMR (DMSO-$d_6$): 6.88 (2 H, d, J=7.6 Hz); 7.26 (1 H, t, J=7.2 Hz); 7.39 (2 H, t, J=7.2 Hz); 7.47 (2 H, d, J=8.4 Hz); 7.56 (2 H, d, J=7.6 Hz).

$^{13}$C-NMR (DMSO-$d_6$): 115.7; 125.9; 126.3; 127.7; 128.8; 128.9; 130.9; 140.2; 157.1.

Stage 2

4-(Dimethylamino-1-ethyl)allophanic acid (4-phenyl)-phenyl ester (US-620)

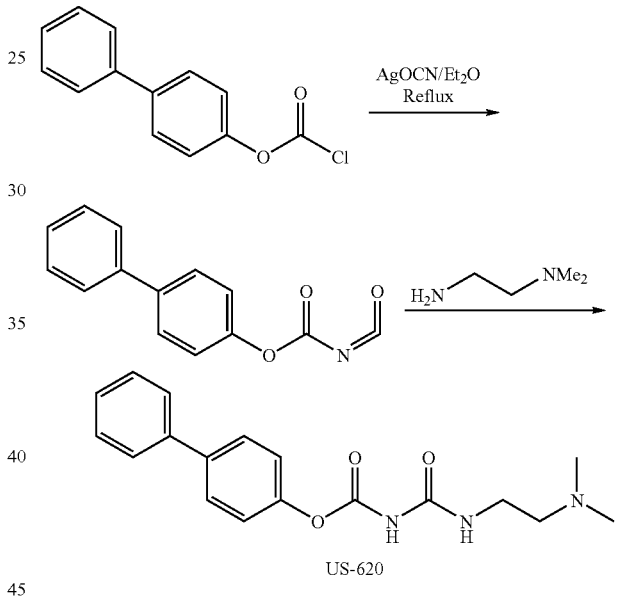

A solution of US-617 (2.70 g, 11.5 mmol) in absolute diethyl ether (20 mL) was added dropwise to a suspension of silver cyanate (2.10 g, 13.8 mmol) in absolute diethyl ether (20 mL) and it was then stirred for 1 h under reflux. After cooling, the precipitated solid was filtered off. The filtrate was added dropwise to a solution of $N^1.N^1$-dimethylethane-1,2-diamine (1.20 g, 1.5 mL, 13.8 mmol) in diethyl ether (25 mL), and the white solid that precipitated was filtered off. The filtrate was concentrated under vacuum. The compound could not be purified by flash chromatography, as it decomposes in the column.

Raw yield: 2.60 g (70%), yellowish, crystalline solid $^1$H-NMR (DMSO-$d_6$): 2.17 (6 H, s); 2.33 (2 H, m); 3.16 (2 H, m); 6.86 (1 H, d, J=8.8 Hz); 7.10-7.80 (9 H, m); 9.57 (1 H, s). Other signals are also present, which do not belong to the compound.

$^1$H-NMR (DMSO-$d_6$): 1 C under DMSO; 45.1; 58.2; 115.6; 121.6; 122.1; 125.2; 125.8; 126.5; 127.4; 127.6; 128.1; 128.7; 150.6; 154.2; 157.0.

Stage 3

4-(Trimethylamino-1-ethyl)allophanic acid (4-phenyl)-phenyl ester iodide (US-624)

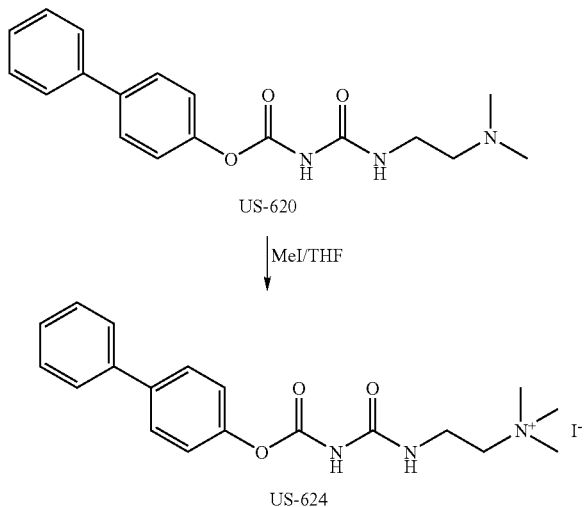

Methyl iodide (560 mg, 240 µL, 4 mmol) was added to a solution of raw US-620 (280 mg, 0.85 mmol) in absolute tetrahydrofuran (20 mL) and it was stirred at room temperature for 5 h. The precipitate was filtered off and dried.

Yield: 247 mg (62%), white solid

Melting point: 95-125° C.

$^1$H-NMR (DMSO-$d_6$, after 3 days): 3.10 (9 H; s); 3.34 (2 H, t, J=6.6 Hz); 3.44 (2 H, br m); 6.66 (1 H, br t); 6.84 (2 H, d, J=8.6 Hz); 7.27 (1 H, t, J=7.0 Hz); 7.40 (2 H, t, J=7.8 Hz); 7.47 (2 H, d, J=8.6 Hz); 7.60 (2 H, d, J=7.0 Hz), 9.55 (1 H, br s).

$^{13}$C-NMR (DMSO-$d_6$, after 3 days): 33.8; 52.6; 64.6; 115.7; 125.9; 126.3; 127.6; 128.7; 130.9; 140.2; 148.5; 157.1; 157.8.

If, in the above reactions, a compound is given two different designations, for example RK324 and IS327, they are different fractions of one and the same compound.

Pharmacological Data:

The test salts according to the invention display excellent affinity for the vanilloid receptor 1 (VR1/TRPV1 receptor). The following table shows the results determined by the aforementioned Method II:

|   | hVR1 10 µM Inhibition | rVR1 10 µM Stimulation | rVR1 10 µM Inhibition | IC50 µM hVR1 | IC50 µM rVR1 |
|---|---|---|---|---|---|
| 1 | 95.44 | 0.55 | 103.15 | 2.43 | 2.1 |
| 2 | 88.93 | −0.02 | 87.13 | 0.92 | 1.23 |
| 3 | 56.92 | −0.73 | 94.41 | 4.27 | 1.27 |
| 13 | 80.84 | 0.36 | 92.11 | 1.1 | 1.3 |
| 14 | 93.08 | 0.09 | 95.54 | 2.4 | 1.15 |
| 15 | 101.37 | −1.01 | 108.94 | 3.45 | 2.95 |
| 16 | 68.63 | 0.58 | 99.30 | 1.7 | 2.9 |

The invention claimed is:

1. A substituted allophanate salt consisting of a cation corresponding to formula I

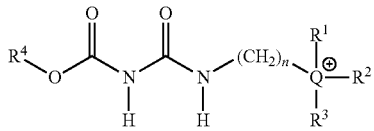

wherein
n =1, 2, 3, 4, 5 or 6;
Q represents N or P;
$R^1$, $R^2$ and $R^3$ each independently denote a linear or branched $C_{1-5}$-alkyl group; or two of $R^1$, $R^2$ and $R^3$ together with the atom Q to which they are bound form a 4-, 5-, 6- or 7-membered, saturated or unsaturated, unsubstituted or mono- or polysubstituted heterocyclic ring, optionally containing one or more further heteroatoms as ring members, and the remaining group $R^1$, $R^2$ or $R^3$ has the meaning given above; and
$R^4$ denotes:
a linear or branched, saturated or unsaturated aliphatic group, which may be unsubstituted or mono- or polysubstituted, and which optionally may contain one or more heteroatoms as units of the chain;
an unsaturated or saturated cycloaliphatic group, which may be unsubstituted or mono- or polysubstituted, and which optionally may contain one or more heteroatoms as ring members, and which optionally may be joined via a linear or branched alkylene group;
an aryl or heteroaryl group, which may be unsubstituted or mono- or polysubstituted, and which optionally may be joined via a linear or branched alkylene group; or
a group —(CH$_2$)$_q$-A$_r$—(CH$_2$)$_s$—B—(CH$_2$)$_t$-C$_u$—R$^5$, wherein
q, s and t each independently denote 0, 1, 2, 3, 4, 5 or 6;
r and u each independently denote 0 or 1;
A and C each independently denote O, S or NH;
B represents:
a linear or branched alkylene, alkenyl or alkinyl group, unsubstituted or mono- or polysubstituted;
an unsaturated or saturated cycloaliphatic group, unsubstituted or mono- or polysubstituted, optionally containing one or more heteroatoms as ring members; or
an aryl or heteroaryl group, unsubstituted or mono- or polysubstituted; and
$R^5$ represents a linear or branched, saturated or unsaturated aliphatic group, unsubstituted or mono- or polysubstituted;
and an anion.

2. A salt according to claim 1, wherein said cation is present in the form of an isolated stereoisomer.

3. A salt according to claim 1, wherein said cation is present in the form of a racemic mixture.

4. A salt according to claim 1, wherein $R^1$, $R^2$ and $R^3$ each independently denote an alkyl group selected from the group consisting of methyl, ethyl, n-propyl and isopropyl; or two of $R^1$, $R^2$ and $R^3$ together with the atom Q to which they are bound form a 4-, 5-, 6- or 7-membered, saturated or unsaturated heterocyclic ring, which may be unsubstituted or mono- or polysubstituted, and which optionally may contain one or more further heteroatoms as ring members, and the remaining group $R^1$, $R^2$ and $R^3$ has the meaning given above.

5. A salt according to claim 1, wherein $R^4$ denotes:

a linear or branched, saturated or unsaturated, unsubstituted or mono- or polysubstituted $C_{1-30}$ aliphatic group;

an unsaturated or saturated 5-, 6- or 7-membered, unsubstituted or mono- or polysubstituted cycloaliphatic group, optionally containing one, two or three heteroatoms as ring members, and optionally bound via a linear or branched $C_{1-3}$-alkylene group;

a 5- or 6-membered, unsubstituted or mono- or polysubstituted aryl or heteroaryl group, optionally bound via a linear or branched $C_{1-3}$-alkylene group; or a group —$(CH_2)_q$—$A_r$—$(CH_2)_s$—B—$(CH_2)_t$—$C_u$—$R^5$, wherein q, s and t each independently denote 0, 1, 2, 3, 4, 5 or 6;

r and u each independently denote 0 or 1;

A and C each independently denote O or S; and

B denotes:

a linear or branched $C_{1-6}$-alkylene, $C_{2-6}$-alkenyl or $C_{2-6}$-alkinyl group, optionally substituted with 1, 2 or 3 substituents independently selected from the group consisting of F, Cl, Br, OH, —O—$C_{1-3}$-alkyl, SH and —S—$C_{1-3}$-alkyl;

a cycloaliphatic or heterocycloaliphatic group selected from the group consisting of cyclopropyl, cyclobutyl, cyclopentyl, cyclohexyl, cyclooctyl, cyclononyl, cyclopentenyl, cyclohexenyl, cycloheptenyl, cyclooctenyl, imidazolinyl, aziridinyl, azetidinyl, pyrrolidinyl, piperidinyl, azepanyl, azokanyl, piperazinyl, tetrahydrofuranyl (tetrahydrofuryl), tetrahydrothienyl (tetrahydrothiophenyl), morpholinyl and thiomorpholinyl; or an aryl or heteroaryl group selected from the group consisting of pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl; and $R^5$ represents a linear or branched, saturated or unsaturated, unsubstituted or mono- or polysubstituted $C_{1-30}$ aliphatic group.

6. A salt according to claim 1, wherein n =1, 2, 3, 4, 5 or 6;

Q represents N or P;

$R^1$, $R^2$ and $R^3$ each independently denote an alkyl group selected from the group consisting of methyl, ethyl, n-propyl and isopropyl; or two of $R^1$, $R^2$ and $R^3$ together with the atom Q to which they are bound form a 4-, 5-, 6- or 7-membered, saturated, unsubstituted heterocyclic ring, and the remaining group $R^1$, $R^2$ or $R^3$ has the meaning given above;

$R^4$ denotes:

a linear or branched, saturated or unsaturated $C_{1-20}$ aliphatic group;

an aryl- or heteroaryl group selected from the group consisting of phenyl, naphthyl, furanyl, thiophenyl and pyridinyl, which optionally may be joined via a $C_{1-3}$-alkylene group, and which may be unsubstituted or substituted with 1, 2, 3, 4 or 5 substituents selected from the group consisting of F, Cl, Br, linear or branched $C_{1-3}$-alkyl, linear or branched $C_{1-3}$-alkoxy, phenyl, phenoxy, benzyl and benzyloxy; or a group —$(CH_2)_q$-$A_r$—$(CH_2)_s$—B—$(CH_2)_t$—$C_u$—$R^5$, wherein q, s and t each independently denote 0, 1 or 2;

r and u each independently denote 0 or 1;

A and C each denote O;

B denotes:

a linear or branched $C_{1-6}$-alkylene, $C_{2-6}$-alkenyl or $C_{2-6}$-alkinyl group; which may be unsubstituted or substituted with 1, 2 or 3 substituents independently selected from the group consisting of F, Cl, Br, OH, —O—$C_{1-3}$-alkyl, SH and —S—$C_{1-3}$-alkyl;

a cycloaliphatic or heterocycloaliphatic group selected from the group consisting of cyclopropyl, cyclobutyl, cyclopentyl, cyclohexyl, cyclooctyl, cyclononyl, cyclopentenyl, cyclohexenyl, cycloheptenyl, cyclooctenyl, imidazolinyl, aziridinyl, azetidinyl, pyrrolidinyl, piperidinyl, azepanyl, azokanyl, piperazinyl, tetrahydrofuranyl (tetrahydrofuryl), tetrahydrothienyl (tetrahydrothiophenyl), morpholinyl and thiomorpholinyl; or an aryl or heteroaryl group selected from the group consisting of pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl, and $R^5$ denotes a linear or branched, saturated or unsaturated $C_{1-20}$ aliphatic group.

7. A salt according to claim 1, wherein the cation corresponds to formula Ia

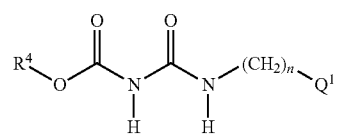

Ia wherein n represents 1, 2 or 3;

$Q^1$ represents a group selected from the group consisting of:

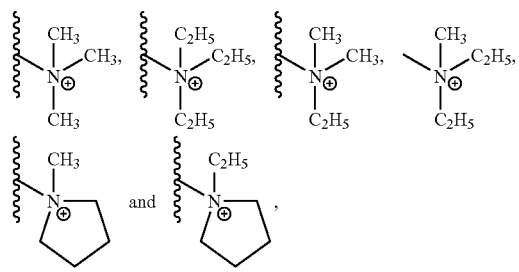

$R^4$ denotes:

a linear or branched $C_{1-20}$ alkyl group;

a phenyl or benzyl group, the cyclic moiety of which may be unsubstituted or substituted with 1, 2, 3, 4 or 5 substituents selected from the group consisting of F, Cl, Br, linear or branched $C_{1-3}$-alkyl, linear or branched $C_{1-3}$-alkoxy, phenyl, phenoxy, benzyl and benzyloxy; or a group selected from the group consisting of:

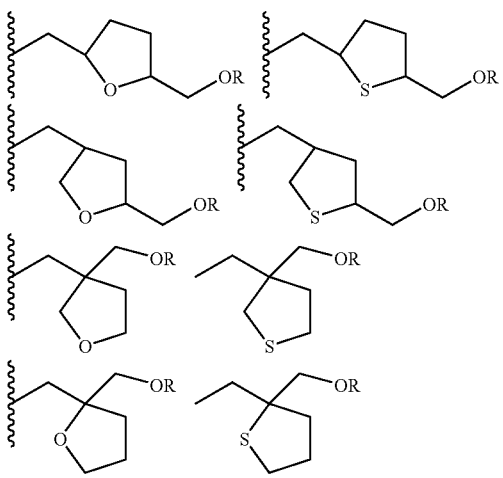

wherein R denotes a linear or branched $C_{1-20}$-alkyl group.

8. A salt according to claim 7, wherein
n represents 1, 2 or 3,
$Q^1$ represents a group selected from the group consisting of:

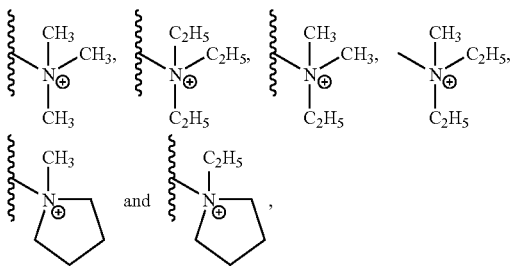

$R^4$ denotes:
an alkyl group selected from the group consisting of methyl, ethyl, n-propyl, n-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl and n-eicosanyl;
a phenyl or benzyl group, the cyclic moiety of which may be unsubstituted or monosubstituted with a substituent selected from the group consisting of F, Cl, Br, linear or branched $C_{1-3}$-alkyl, linear or branched $C_{1-3}$-alkoxy, phenyl, phenoxy, benzyl and benzyloxy; or
a group corresponding to one of the following formulas:

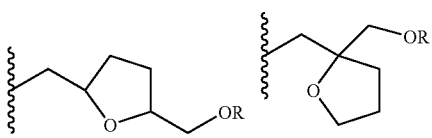

wherein R denotes an alkyl group selected from the group consisting of methyl, ethyl, n-propyl, n-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl and n-eicosanyl.

9. A salt according to claim 1, wherein said anion is a halide ion or a hydroxyl ion.

10. A salt according to claim 9, wherein said anion is a chloride, bromide or iodide ion.

11. A salt according to claim 1, selected from the group consisting of:
[1] 4-(trimethylamino-1-ethyl)allophanic acid dodecyl ester iodide,
[2] 4-(pyrrolidinium-1-ethyl)allophanic acid hexadecyl ester iodide,
[3] 4-(trimethylamino-1-propyl)allophanic acid hexadecyl ester iodide,
[4] 4-(trimethylamino-1-ethyl)allophanic acid octyl ester iodide,
[5] 4-(trimethylamino-1-ethyl)allophanic acid butyl ester iodide,
[6] 4-(trimethylamino-1-ethyl)allophanic acid phenyl ester iodide,
[7] 4-benzyloxycarbonyl4-(N-methyldimethylammonium-1-ethyl)allophanic acid benzyl ester iodide,
[8] 4-(trimethylamino-1-ethyl)allophanic acid benzyl ester iodide,
[9] 4-(trimethylamino-1-ethyl)allophanic acid (4-phenyl)-phenyl ester iodide,
[10] 4-(trimethylamino-1-ethyl)allophanic acid ethyl ester iodide,
[11] 4-(trimethylamino-1-ethyl)allophanic acid butyl ester iodide,
[12] 4-(trimethylamino-1-ethyl)allophanic acid hexyl ester iodide,
[13] 4-(trimethylamino-1-ethyl)allophanic acid (cis-5-hexadecyloxymethyltetrahydrofuran-2-yl)methyl ester iodide,
[14] 4-(trimethylamino-1-ethyl)allophanic acid 3-hexadecyloxy-2-methoxypropan-1-yl ester iodide,
[15] 4-(trimethylamino-1-ethyl)allophanic acid hexadecyl ester iodide, and
[16] 4-(trimethylamino-1-ethyl)allophanic acid (2-hexadecyloxymethyltetrahydro-furan-2-yl)methyl ester iodide.

12. A process for producing a substituted allophanate according to claim 1, said process comprising:
reacting a compound corresponding to formula II

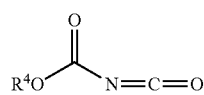

wherein $R^4$ has the meaning given in claim 1,
in a reaction medium, optionally in the presence of a base, with a compound corresponding to formula III

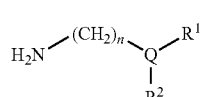

wherein n, $R^1$ and $R^2$ have the meanings given in claim 1, to obtain a compound of formula III'

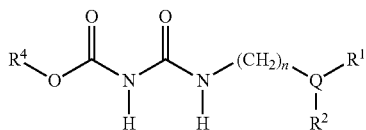

wherein $R^1$, $R^2$, $R^4$ and n have the meanings given above, and reacting the obtained compound of formula III' with an alkylating agent to obtain a compound of formula I.

13. A pharmaceutical composition comprising a salt according to claim 1, and at least one physiologically compatible excipient.

14. A method of treating or inhibiting a disorder or disease state selected from the group consisting of pain; arthralgia; migraine; neurodegenerative diseases selected from the group consisting of multiple sclerosis, Alzheimer's disease, Parkinson's disease and Huntington's disease; epilepsy; asthma; cough; urinary incontinence; overactive bladder; gastric ulcers; irritable bowel syndrome; diarrhea; pruritus; and eating disorders selected from the group consisting of bulimia, cachexia, anorexia and obesity; or for diuresis; antinatriuresis; increasing alertness; increasing libido; modulating motor activity; reducing anxiety; or effecting local anaesthesia, in a subject in need thereof, said method comprising administering to said subject a therapeutically effective amount of a salt according to claim 1.

15. A method according to claim 14, wherein said disorder is selected from the group consisting of acute pain, chronic pain, neuropathic pain and visceral pain.

* * * * *